(12) United States Patent
Mamishin et al.

(10) Patent No.: US 12,277,266 B2
(45) Date of Patent: Apr. 15, 2025

(54) LINE-OF-SIGHT DETECTION DEVICE, DISPLAY DEVICE, AND METHOD FOR SENSING EYEBALL

(71) Applicant: SONY GROUP CORPORATION, Tokyo (JP)

(72) Inventors: Yuki Mamishin, Tokyo (JP); Ryo Ogawa, Tokyo (JP); Takuro Noda, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 18/246,078

(22) PCT Filed: Sep. 14, 2021

(86) PCT No.: PCT/JP2021/033616
§ 371 (c)(1),
(2) Date: Mar. 21, 2023

(87) PCT Pub. No.: WO2022/080058
PCT Pub. Date: Apr. 21, 2022

(65) Prior Publication Data
US 2023/0367393 A1    Nov. 16, 2023

(30) Foreign Application Priority Data
Oct. 13, 2020    (JP) ................. 2020-172360

(51) Int. Cl.
*G06F 3/01*    (2006.01)
*G02B 27/00*    (2006.01)
(Continued)

(52) U.S. Cl.
CPC ......... *G06F 3/013* (2013.01); *G02B 27/0093* (2013.01); *G02B 27/0172* (2013.01); *H04N 25/134* (2023.01); *G02B 2027/0138* (2013.01)

(58) Field of Classification Search
None
See application file for complete search history.

(56) References Cited

U.S. PATENT DOCUMENTS 5,298,927 A * 3/1994 Konishi ................ G03B 13/02
351/200
2019/0244005 A1 8/2019 Suzuki et al.
2020/0026349 A1 1/2020 Fontanel et al.

FOREIGN PATENT DOCUMENTS

| JP | 2015-013031 A | 1/2015 |
| JP | 2018-197974 A | 12/2018 |
| WO | 2019/067731 A1 | 4/2019 |

OTHER PUBLICATIONS

International Search Report and Written Opinion of PCT Application No. PCT/JP2021/033616, issued on Nov. 16, 2021, 09 pages of ISRWO.

\* cited by examiner

*Primary Examiner* — Brian M Butcher
(74) *Attorney, Agent, or Firm* — CHIP LAW GROUP

(57) ABSTRACT

To provide a line-of-sight detection device capable of further improving line-of-sight detection accuracy, achieving low latency, and achieving low power consumption. Provided is a line-of-sight detection device that includes an imaging element having an event-driven function, a first mode generation unit that generates a Purkinje detection mode, a second mode generation unit that generates a pupil detection mode, and a third mode generation unit that generates an event-driven mode.

22 Claims, 14 Drawing Sheets

(51) Int. Cl.
*G02B 27/01* (2006.01)
*H04N 25/13* (2023.01)

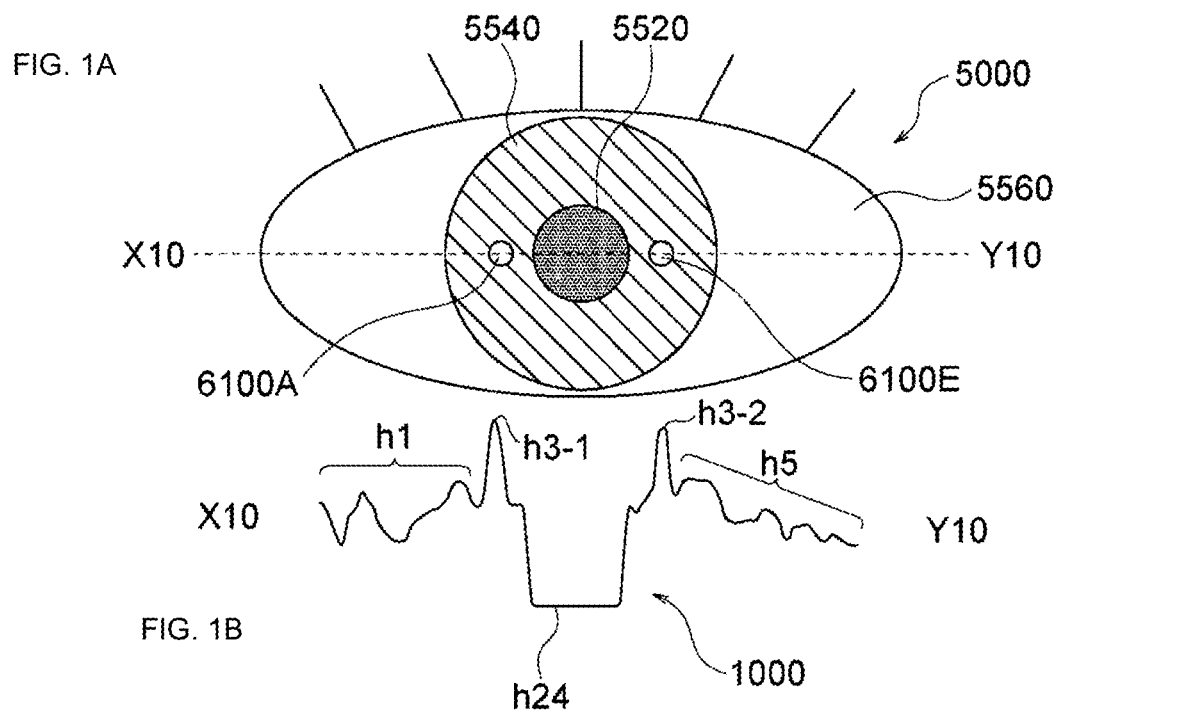
FIG. 1A
FIG. 1B
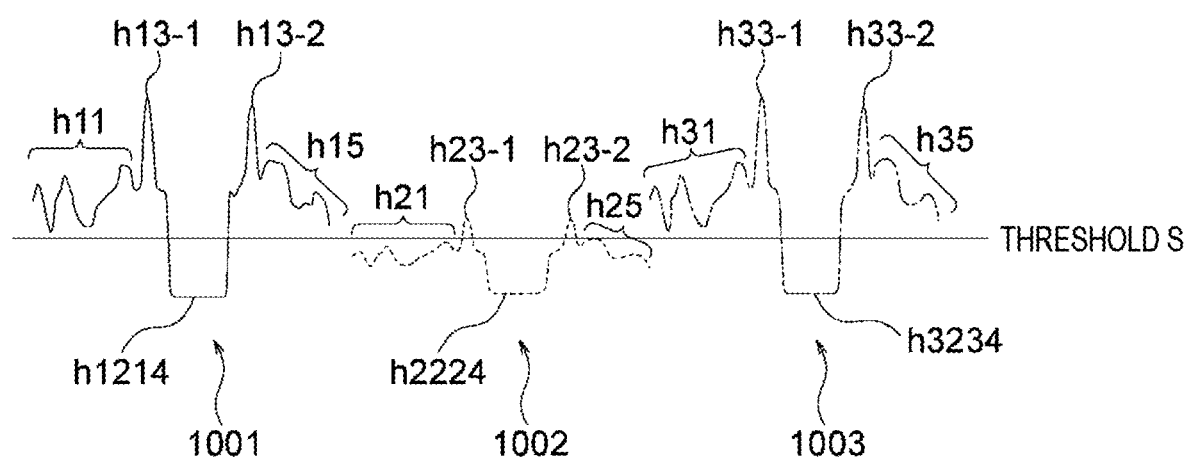
FIG. 2

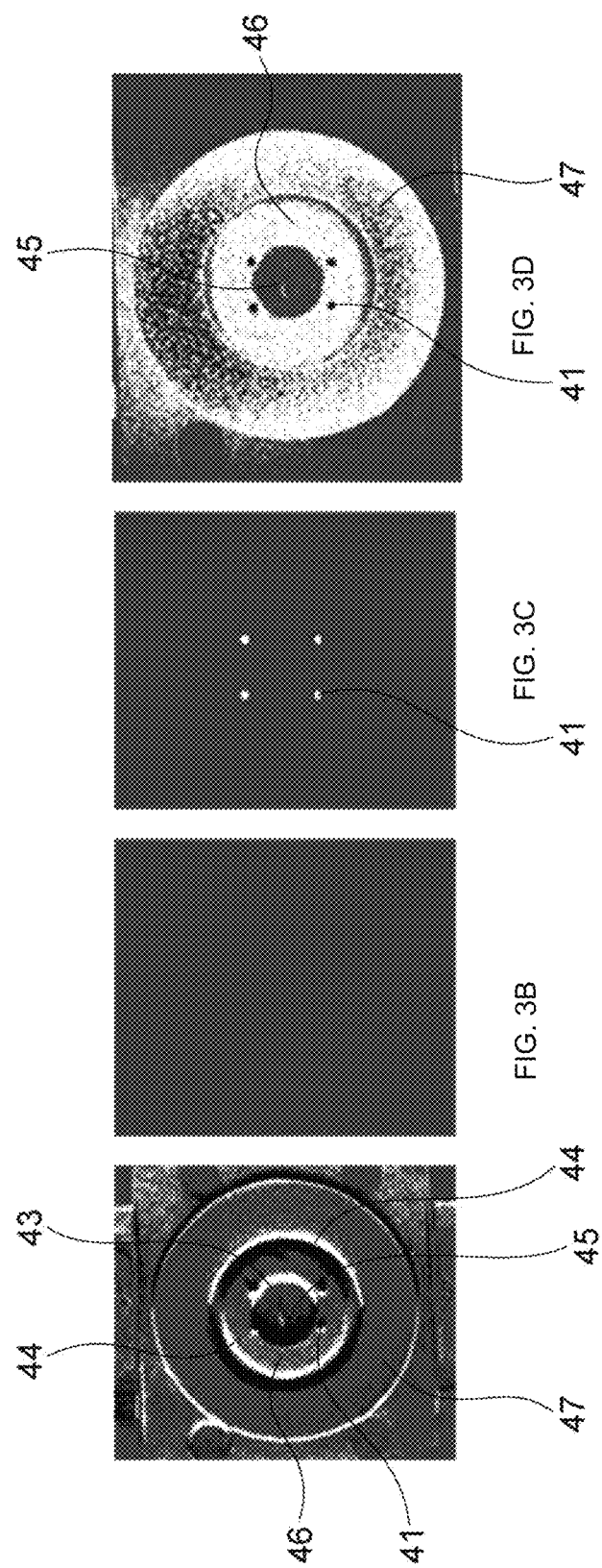

LINE-OF-SIGHT DETECTION DEVICE, DISPLAY DEVICE, AND METHOD FOR SENSING EYEBALL

CROSS REFERENCE TO RELATED APPLICATIONS

This application is a U.S. National Phase of International Patent Application No. PCT/JP2021/033616 filed on Sep. 14, 2021, which claims priority benefit of Japanese Patent Application No. JP 2020-172360 filed in the Japan Patent Office on Oct. 13, 2020. Each of the above-referenced applications is hereby incorporated herein by reference in its entirety.

TECHNICAL FIELD

The present technology relates to a line-of-sight detection device, a display device, and a method for sensing an eyeball.

BACKGROUND ART

Various development destinations of sensing of eyeball information are expected. Neuroscience, bioengineering, and medicine are expected in the research field, and transmission of techniques through line-of-sight tracking, improvement of usability of UX, and the like are expected in the industrial field, and furthermore, development to security by iris authentication is also expected. In recent years, head-mounted displays (AR/VR), which have been increasingly and competitively developed, have been used for foveated rendering and expansion of viewable areas (eye-boxes).

For example, in Patent Document 1, two states of the Purkinje detection (a luminance state modulation time) and pupil detection (event-driven time) are created by using two types of luminance states.

CITATION LIST

Patent Document

Patent Document 1: International Publication No. 2019/067731

SUMMARY OF THE INVENTION

Problems to be Solved by the Invention

In a technology proposed in Patent Document 1, however, there is a possibility that it is difficult to achieve further improvement in line-of-sight detection accuracy, achieve low latency, and achieve low power consumption.

Therefore, the present technology has been made in view of such a circumstance, and a main object thereof is to provide a line-of-sight detection device, a display device including the line-of-sight detection device, and a method for sensing an eyeball, which enable achievement of further improvement in line-of-sight detection accuracy, achievement of low latency, and achievement of low power consumption.

Solutions to Problems

As a result of intensive research to accomplish the above-described object, the present inventors have surprisingly succeeded in achieving further improvement in line-of-sight detection accuracy, achieving low latency, and achieving low power consumption, and have completed the present technology.

That is, as a first aspect, the present technology provides a line-of-sight detection device including:
an imaging element having an event-driven function;
a first mode generation unit that generates a Purkinje detection mode;
a second mode generation unit that generates a pupil detection mode; and
a third mode generation unit that generates an event-driven mode.

The line-of-sight detection device as the first aspect according to the present technology may further include a light emitting device, and in this case,
the light emitting device may have three light emission intensities.

The line-of-sight detection device as the first aspect according to the present technology may further include a light emitting device, and in this case,
the light emitting device may have two light emission intensities,
the imaging element having the event-driven function may include a first pixel and a second pixel which have different thresholds, and
the first pixel and the second pixel may be arranged in a Bayer array.

The line-of-sight detection device as the first aspect according to the present technology may further include a light emitting device, and in this case,
the light emitting device may have two light emission intensities, and
the imaging element having the event-driven function may have two thresholds with change of time.

The line-of-sight detection device as the first aspect according to the present technology may further include a plurality of light emitting devices, and in this case,
the first mode generation unit may generate the Purkinje detection mode when each of the plurality of light emitting devices is sequentially turned on.

The line-of-sight detection device as the first aspect according to the present technology may further include a light emitting device, and in this case,
the light emitting device may have three light emission intensities,
the three light emission intensities may be a high intensity, a medium intensity, and a low intensity, and
an intensity difference between the high intensity and the medium intensity may be substantially identical to an intensity difference between the medium intensity and the low intensity.

The line-of-sight detection device as the first aspect according to the present technology may further include a plurality of light emitting devices, and in this case,
the plurality of light emitting devices may change light emission intensities substantially simultaneously, and
the second mode generation unit may generate the pupil detection mode.

The line-of-sight detection device as the first aspect according to the present technology may further include: a light emitting device; and a signal acquisition unit, and
the signal acquisition unit may acquire a signal in synchronization with a time stamp of a change in a light emission intensity of the light emitting device in the Purkinje detection mode and the pupil detection mode, and may perform time stamp accumulation to acquire a signal in the event-driven mode.

In the line-of-sight detection device as the first aspect according to the present technology,
the second mode generation unit may generate the pupil detection mode when detection is lost in the event-driven mode.

In the line-of-sight detection device as the first aspect according to the present technology,
the second mode generation unit may generate the pupil detection mode when a detection likelihood of the event-driven mode is less than a predetermined value.

In the line-of-sight detection device as the first aspect according to the present technology,
the second mode generation unit may generate the pupil detection mode when an end of a saccade is detected in the event-driven mode.

As a second aspect, the present technology provides
a display device including at least the line-of-sight detection device as the first aspect according to the present technology.

As a third aspect, the present technology provides
a method for sensing an eyeball including:
by using an imaging element having an event-driven function,
generating a Purkinje detection mode, generating a pupil detection mode, and generating an event-driven mode; and
transitioning to the Purkinje detection mode, transitioning to the pupil detection mode, and transitioning to the event-driven mode.

The method for sensing an eyeball as the third aspect according to the present technology may further include changing to three light emission intensity states using a light emitting device.

The method for sensing an eyeball as the third aspect according to the present technology may further include changing to two light emission intensity states using a light emitting device, and in this case,
the imaging element having the event-driven function may include a first pixel and a second pixel which have different thresholds, and
the first pixel and the second pixel may be arranged in a Bayer array.

The method for sensing an eyeball as the third aspect according to the present technology may further include changing to two light emission intensity states using a light emitting device, and in this case,
the imaging element having the event-driven function may have two thresholds with change of time.

The method for sensing an eyeball as the third aspect according to the present technology may further include sequentially transitioning to the Purkinje detection mode by sequentially turning on each of a plurality of light emitting devices using the plurality of light emitting devices.

The method for sensing an eyeball as the third aspect according to the present technology may further include changing to three light emission intensity states using a light emitting device, and in this case,
the three light emission intensities may be a high intensity, a medium intensity, and a low intensity, and
an intensity difference between the high intensity and the medium intensity may be substantially identical to an intensity difference between the medium intensity and the low intensity.

The method for sensing an eyeball as the third aspect according to the present technology may further include substantially simultaneously changing light emission intensities of a plurality of light emitting devices using the plurality of light emitting devices to transition to the pupil detection mode The method for sensing an eyeball as the third aspect according to the present technology may further include:
acquiring a signal in synchronization with a time stamp of a change in a light emission intensity of a light emitting device in the Purkinje detection mode and the pupil detection mode; and
performing time stamp accumulation to acquire a signal in the event-driven mode.

The method for sensing an eyeball as the third aspect according to the present technology may further include transitioning to the pupil detection mode when detection is lost in the event-driven mode.

The method for sensing an eyeball as the third aspect according to the present technology may further include transitioning to the pupil detection mode when a detection likelihood of the event-driven mode is less than a predetermined value.

The method for sensing an eyeball as the third aspect according to the present technology may further include transitioning to the pupil detection mode when an end of a saccade is detected in the event-driven mode.

According to the present technology, the further improvement of the line-of-sight detection accuracy, the low latency, and the low power consumption can be achieved. Note that the effects described herein are not necessarily limited, and may be any of effects described in the present disclosure.

BRIEF DESCRIPTION OF DRAWINGS

FIGS. 1A and 1B are views for describing an intensity distribution of reflected light of an eye.

FIG. 2 is a view illustrating a relationship between a threshold of a dynamic vision sensor (DVS) and a Purkinje detection mode, a pupil detection mode, and an event-driven mode.

FIGS. 3A, 3B, 3C, and 3D are views illustrating an image when an eyeball is sensed using a line-of-sight detection device in a first embodiment to which the present technology is applied.

MODE FOR CARRYING OUT THE INVENTION

Figure 4A:
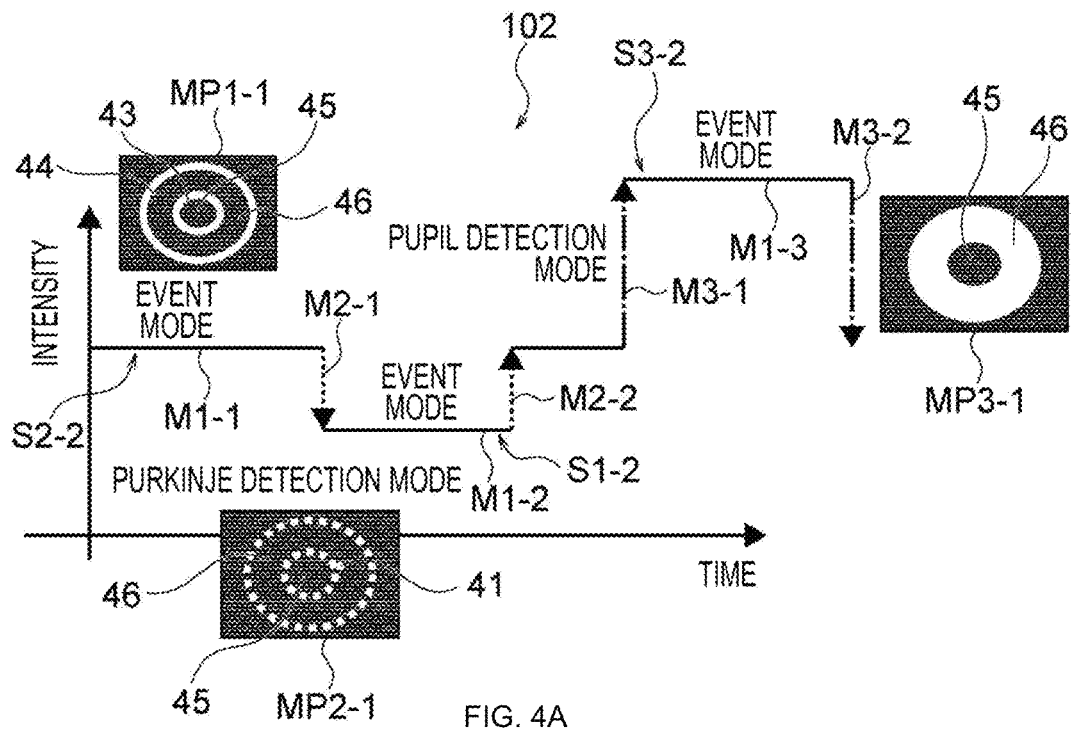
FIGS. 4A and 4B are views illustrating an example of a transition method of three modes (Purkinje detection mode, pupil detection mode, and event-driven mode) in a line-of-sight detection device and a method for sensing an eyeball in a second embodiment to which the present technology is applied.

Hereinafter, preferred modes for carrying out the present technology will be described. The embodiments to be described hereinafter illustrate examples of representative embodiments of the present technology, and the scope of the present technology is not narrowly construed by the embodiments. Note that, in the drawings, "upper" means an upper direction or an upper side in the drawings, "lower" means a lower direction or a lower side in the drawings, "left" means a left direction or a left side in the drawings, and "right" means a right direction or a right side in the drawings unless otherwise specified. Furthermore, in the description using the drawings, the same or equivalent elements or members are denoted by the same reference signs, and the redundant description is omitted.

Note that a description will be given in the following order.

1. Overview of Present Technology
2. First Embodiment (Example 1 of Line-of-Sight Detection Device and Example 1 of Method for Sensing Eyeball)
3. Second Embodiment (Example 2 of Line-of-Sight Detection Device and Example 2 of Method for Sensing Eyeball)
4. Third Embodiment (Example 3 of Line-of-Sight Detection Device and Example 3 of Method for Sensing Eyeball)
5. Fourth Embodiment (Example 4 of Line-of-Sight Detection Device and Example 4 of Method for Sensing Eyeball)
6. Fifth Embodiment (Example 5 of Line-of-Sight Detection Device and Example 5 of Method for Sensing Eyeball)
7. Sixth Embodiment (Example 6 of Line-of-Sight Detection Device and Example 6 of Method for Sensing Eyeball)
8. Seventh Embodiment (Example 7 of Line-of-Sight Detection Device and Example 7 of Method for Sensing Eyeball)
9. Eighth Embodiment (Example 8 of Line-of-Sight Detection Device and Example 8 of Method for Sensing Eyeball)
10. Ninth Embodiment (Example 9 of Line-of-Sight Detection Device and Example 9 of Method for Sensing Eyeball)
11. Tenth Embodiment (Example 10 of Line-of-Sight Detection Device and Example 10 of Method for Sensing Eyeball)
12. Eleventh Embodiment (Example 1 of Display Device)

1. Overview of Present Technology

First, an overview of the present technology will be described. The present technology relates to a line-of-sight detection device, a display device, and a method for sensing an eyeball.

In general, camera-based techniques are used in eye sensing, and among them, a pupil and cornea detection method is a general line-of-sight detection method. In this line-of-sight detection method, it is important to distinguish and appropriately label a plurality of beams of corneal reflection light, and for example, there is a technical example in which beams of corneal reflection light are sequentially turned on to improve the labeling accuracy. Furthermore, in a camera system, power saving and latency are sometimes problems, but a DVS is in the technical example to solve the problems. In the technical example, however, when the DVS is used, event firing occurs for not only a Purkinje image but also other components such as a pupil unless an appropriate intensity is selected so that latency such as data congestion may occur. When the pupil is detection only by an event, the pupil is likely to be lost in a situation, for example, where the pupil has moved at the time of blinking or the like.

The present technology has been made in view of such a circumstance. The present technology can generate three characteristic modes (Purkinje detection mode, pupil detection mode, and event-driven mode) by using a relationship between a threshold of an imaging element having an event-driven function and an intensity pattern of reflected light of an eye.

According to the present technology, the further improvement of the line-of-sight detection accuracy, the low latency, and the low power consumption can be achieved.

Hereinafter, preferred embodiments for carrying out the present technology will be described in detail with reference to the drawings. The embodiments to be described hereinafter illustrate examples of representative embodiments of the present technology, and the scope of the present technology is not narrowly construed by the embodiments. Note that, in the description using the drawings, the same or

2. First Embodiment (Example 1 of Line-of-Sight Detection Device and Example 1 of Method for Sensing Eyeball)

A line-of-sight detection device in a first embodiment (Example 1 of the line-of-sight detection device) according to the present technology is a line-of-sight detection device including: an imaging element (for example, dynamic vision sensor (DVS)) having an event-driven function; a first mode generation unit that generates a Purkinje detection mode (sometimes referred to simply as a Purkinje mode, and the same applies hereinafter); a second mode generation unit that generates a pupil detection mode (sometimes referred to simply as a pupil mode); and a third mode generation unit that generates an event-driven mode (sometimes referred to simply as an event mode, and the same applies hereinafter).

A method for sensing an eyeball in the first embodiment (Example 1 of the method for sensing an eyeball) according to the present technology is a method for sensing an eyeball including: by using an imaging element having an event-driven function, generating a Purkinje detection mode, generating a pupil detection mode, and generating an event-driven mode; and transitioning to the Purkinje detection mode, transitioning to the pupil detection mode, and transitioning to the event-driven mode. Meanwhile, the method for sensing an eyeball in the first embodiment (Example 1 of the method for sensing an eyeball) according to the present technology may be executed using the line-of-sight detection device in the first embodiment (Example 1 of the line-of-sight detection device) according to the present technology.

The line-of-sight detection device and the method for sensing an eyeball in the first embodiment according to the present technology will be described with reference to FIGS. 1A, 1B, 2, 3A, 3B, 3C, and 3D.

FIGS. 1A and 1B are views for describing an intensity distribution of reflected light of an eye. More specifically, FIG. 1A is a view illustrating a configuration of the eye, and FIG. 1B is a view illustrating an intensity pattern 1000 of reflected light of an eye 5000 at the time of being cut along a line X10-Y10 illustrated in FIG. 1A. FIG. 2 is a view illustrating a relationship between a threshold of the dynamic vision sensor (DVS) and the Purkinje detection mode generated in a first mode, the pupil detection mode generated in a second mode, and the event-driven mode generated in a third mode. FIGS. 3A, 3B, 3C, and 3D are views illustrating an image when an eyeball is sensed using the line-of-sight detection device in the first embodiment according to the present technology.

The eye 5000 illustrated in FIG. 1A includes a pupil 5520, an iris 5540, a cornea 5500 covering the pupil 5520 and the iris 5540, and a sclera 5560. In the eye 5000, Purkinje images (reflected light on the surface of the cornea 5500) 6100A and 6100E are detected. As illustrated in the intensity pattern 1000 of reflected light of the eye in FIG. 1B, under infrared light, there is a relationship of intensities (reflectances) of reflected light that corneal reflection (Purkinje image) (h3)>iris (h1 and h5)>pupil (h24). Note that FIG. 1B illustrates that the intensity (reflectance) of reflected light is high on the upper side of FIG. 1B.

FIG. 2 illustrates an intensity pattern 1001 of reflected light of the eye in the event-driven mode, an intensity pattern 1002 of reflected light of the eye in the Purkinje detection mode, and an intensity pattern 1003 of reflected light of the eye in the pupil detection mode. As the intensity pattern 1001 of reflected light of the eye in the event-driven mode, reflected light h11 and h15 of the iris, reflected light h13-1 and 13-2 of the Purkinje image, and reflected light h1214 of the pupil are illustrated. As the intensity pattern 1002 of reflected light of the eye in the Purkinje detection mode, reflected light h21 and h25 of the iris, reflected light h23-1 and 23-2 of the Purkinje image, and reflected light h2224 of the pupil are illustrated. As the intensity pattern 1003 of reflected light of the eye in the pupil detection mode, reflected light h31 and h35 of the iris, reflected light h33-1 and 33-2 of the Purkinje image, and reflected light h3234 of the pupil are illustrated. Note that FIG. 2 illustrates that the intensity of reflected light is high on the upper side of FIG. 2.

As indicated by the intensity pattern 1002 of reflected light of the eye in the Purkinje detection mode, only the Purkinje is fired when only the reflected light (h23-1 and h23-2) of the Purkinje exceeds a threshold S. On the other hand, when the reflected light (h11, h13-1, h13-2, h15, h31, h33-1, h33-2, and h35) of the iris exceeds the threshold S, the reflected light of the iris and the reflected light of the Purkinje are fired. This firing includes firing caused by an event and forced firing caused by a change in illumination light. When the forced firing occurs, event data for all of the Purkinje and the pupil are output. On the other hand, in the case of the event firing, only edge portions (for example, a boundary (edge) 43 between the pupil 45 and the iris 46 and a boundary (edge) 44 between the iris 46 and the sclera 47) are fired (see also FIGS. 3A, 3B, 3C, and 3D as described later).

In FIGS. 3A, 3B, 3C, and 3D, FIG. 3A illustrates an image at the time of sensing the eyeball when the eyeball has moved in the event-driven mode using the line-of-sight detection device in the first embodiment according to the present technology; FIG. 3B illustrates an image at the time of sensing the eyeball when the eyeball is not moving in the event-driven mode; FIG. 3C illustrates an image at the time of sensing the eyeball in the Purkinje detection mode; and FIG. 3D illustrates an image at the time of sensing the eyeball in the pupil detection mode.

In FIG. 3A (event-driven mode), the eyeball is moving, and thus, the boundary (edge) 44 between the iris 46 and the sclera 47 and the boundary (edge) 43 between the pupil 45 and the iris 46 are fired as events. In FIG. 3B (event-driven mode), the eyeball is not moving, and thus, the boundary (edge) 44 between the iris 46 and the sclera 47, the boundary (edge) 43 between the pupil 45 and the iris 46, and the like are not fired as events, and a solid image of an achromatic color such as gray is obtained. In FIG. 3C (Purkinje detection mode), only a Purkinje image 41 is fired. In FIG. 3D (pupil detection mode), all of the Purkinje image 41, the pupil 45, the iris 46, and the sclera 47 are forcibly fired. Note that firing refers to outputting an event (generating a signal) when a change in an optical signal exceeds a predetermined threshold in each pixel included in the imaging element having the event-driven function.

In the three modes (event-driven mode, Purkinje detection mode, and pupil detection mode), for example, the pupil is constantly detected in the event-driven mode so that the speed can be increased, and high robustness and high accuracy can be achieved by setting the pupil detection mode when the pupil is lost. Furthermore, highly accurate line-of-sight detection is possible by setting the Purkinje detection mode.

As described above, contents that have been described regarding the line-of-sight detection device and the method for sensing an eyeball in the first embodiment (Example 1 of the line-of-sight detection device and Example 1 of the method for sensing an eyeball) according to the present technology can be applied to line-of-sight detection devices and methods for sensing an eyeball in second to tenth embodiments according to the present technology as described later particularly as long as there is no technical contradiction.

3. Second Embodiment (Example 2 of Line-of-Sight Detection Device and Example 2 of Method for Sensing Eyeball)

The line-of-sight detection device in the second embodiment (Example 2 of the line-of-sight detection device) according to the present technology is a line-of-sight detection device including: an imaging element (for example, a dynamic vision sensor (DVS)) having an event-driven function; a first mode generation unit that generates a Purkinje detection mode; a second mode generation unit that generates a pupil detection mode; and a third mode generation unit that generates an event-driven mode, and further includes a light emitting device. The light emitting device provided in the line-of-sight detection device in the second embodiment according to the present technology has three light emission intensities.

The method for sensing an eyeball in the second embodiment (Example 2 of the method for sensing an eyeball) according to the present technology is a method for sensing an eyeball including: by using an imaging element having an event-driven function, generating a Purkinje detection mode, generating a pupil detection mode, and generating an event-driven mode; and transitioning to the Purkinje detection mode, transitioning to the pupil detection mode, and transitioning to the event-driven mode, and further includes changing to three light emission intensity states using a light emitting device. Meanwhile, the method for sensing an eyeball in the second embodiment (Example 2 of the method for sensing an eyeball) according to the present technology may be executed using the line-of-sight detection device in the second embodiment (Example 2 of the line-of-sight detection device) according to the present technology.

Then, in the method for sensing an eyeball in the second embodiment (Example 2 of the method for sensing an eyeball) according to the present technology, a transition is made from the Purkinje detection mode to the event-driven mode, a transition is made from the event-driven mode to the Purkinje detection mode, a transition is made from the pupil detection mode to the event-driven mode, a transition is made from the event-driven mode to the pupil detection mode, and a transition is made from the Purkinje detection mode to the pupil detection mode.

The line-of-sight detection device and the method for sensing an eyeball in the second embodiment according to the present technology will be described with reference to FIGS. 4A and 4B.

Figure 4B:
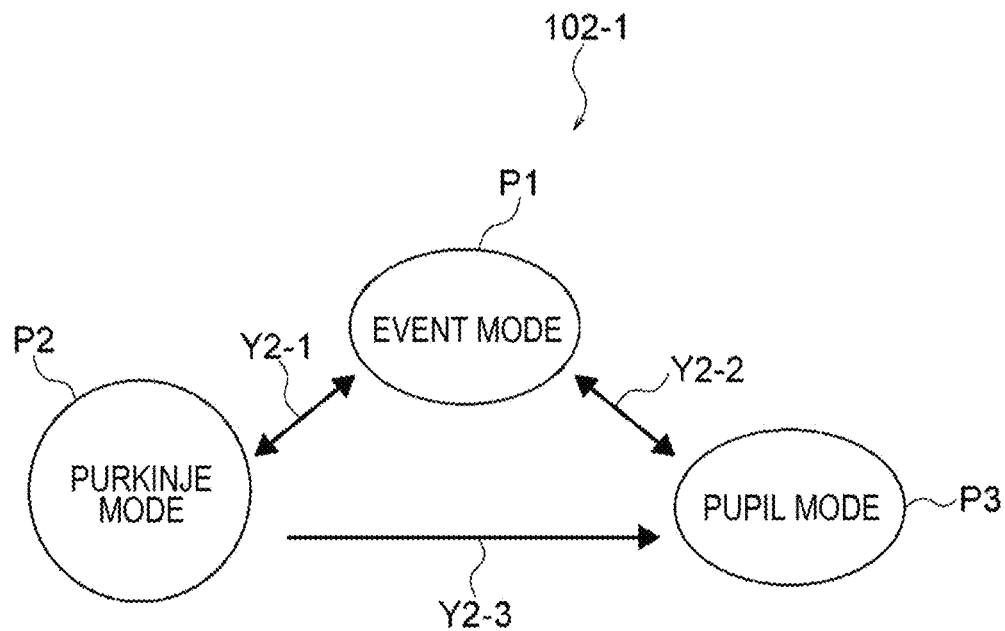

FIGS. 4A and 4B are views illustrating an example of a transition method of three modes (the Purkinje detection mode, the pupil detection mode, and the event-driven mode) in the line-of-sight detection device and the method for sensing an eyeball in the second embodiment according to the present technology. More specifically, FIG. 4A is a view illustrating a transition pattern 102 of the three modes (Purkinje detection mode, pupil detection mode, and event-driven mode). In FIG. 4A, the horizontal axis represents time, and the vertical axis represents a light emission intensity of the light emitting device (for example, an LED). FIG. 4B is a view (also referred to as a state shift diagram 102-1) summarizing a transition relationship (indicated by reference sign 102-1) of the three modes (Purkinje detection mode, pupil detection mode, and event-driven mode).

In the transition pattern 102, a transition is made from an event mode M1-1 in a state where the intensity is constant at a medium intensity S2-2 to a Purkinje mode M2-1 that is a moment when the intensity changes from the medium intensity S2-2 to a low intensity S1-2, subsequently, a transition is made to an event mode M1-2 in a state where the intensity is constant at the low intensity S1-2, and a transition is made to a Purkinje mode M2-2 that is a moment when the intensity changes from the low intensity S1-2 to the medium intensity S2-2. Then, a transition is made from the Purkinje mode M2-2 to an event mode M1-1-1 in a state where the intensity is constant at the medium intensity S2-2, subsequently, a transition is made to a pupil mode M3-1 that is a moment when the intensity changes from the medium intensity S2-2 to a high intensity S3-2, a transition is made from the pupil mode M3-1 to an event mode M1-3 in a state where the intensity is constant at the high intensity S3-2, and further, a transition is made to a pupil mode M3-2 that is a moment when the intensity changes from the high intensity S3-2 to the medium intensity S2-2 again.

As described above, the transition pattern 102 has the three intensities, that is, the low intensity S1-2, the medium intensity S2-2, and the high intensity S3-2. In a section (event mode) in which each intensity (the low intensity S1-2, the medium intensity S2-2, or the high intensity S3-2) is constant, reflected light of the pupil and Purkinje (Fresnel reflection and diffuse reflection components) is triggered with respect to movement of the eyeball.

At the moment when a transition is made from the central intensity S2-2 to the low intensity S1-2 with a small displacement (the moment when the intensity changes) or the moment when a transition is made from the low intensity S1-2 to the medium intensity S2-2 with a small displacement (the moment when the intensity changes) (in the Purkinje detection mode), the intensity of light is forcibly changed, and only a reflective displacement amount of Purkinje light (Fresnel reflection component) is triggered.

At the moment when a transition is made from the medium intensity S2-2 to the high intensity S3-2 with a large displacement (the moment when the intensity changes) or the moment when a transition is made from the high intensity S3-2 to the medium intensity S2-2 with a large displacement (the moment when the intensity changes) (in the pupil detection mode), the intensity of light is forcibly changed, and reflective displacement amounts of reflected light of the pupil and the Purkinje (Fresnel reflection and diffuse reflection components) are triggered.

As illustrated in the state shift diagram 102-1, in the transition pattern 102, it is possible to transition from an event mode P1 to a Purkinje mode P2, and to transition from the Purkinje mode P2 to the event mode P1 (an arrow Y2-1 illustrated in FIG. 4B). Furthermore, in the transition pattern 102, it is possible to transition from the event mode P1 to a pupil mode P3, and to transition from the pupil mode P3 to the event mode P1 (an arrow Y2-2 illustrated in FIG. 4B). Moreover, in the transition pattern 102, it is possible to transition from the Purkinje mode P2 to the pupil mode P3 (an arrow Y2-3 illustrated in FIG. 4B).

As described above, contents that have been described regarding the line-of-sight detection device and the method for sensing an eyeball in the second embodiment (Example 2 of the line-of-sight detection device and Example 2 of the method for sensing an eyeball) according to the present technology can be applied to the line-of-sight detection device and the method for sensing an eyeball in the first embodiment according to the present technology described above, and the line-of-sight detection devices and the methods for sensing an eyeball in the third to tenth embodiments according to the present technology as described later particularly as long as there is no technical contradiction.

4. Third Embodiment (Example 3 of Line-of-Sight Detection Device and Example 3 of Method for Sensing Eyeball)

The line-of-sight detection device in the third embodiment (Example 3 of the line-of-sight detection device) according to the present technology is a line-of-sight detection device including: an imaging element (for example, a dynamic vision sensor (DVS)) having an event-driven function; a first mode generation unit that generates a Purkinje detection mode; a second mode generation unit that generates a pupil detection mode; and a third mode generation unit that generates an event-driven mode, and further includes a light emitting device. The light emitting device provided in the line-of-sight detection device in the third embodiment according to the present technology has three light emission intensities. The three light emission intensities are a high intensity, a medium intensity, and a low intensity, and an intensity difference between the high intensity and the medium intensity is substantially identical to an intensity difference between the medium intensity and the low intensity.

The method for sensing an eyeball in the third embodiment (Example 3 of the method for sensing an eyeball) according to the present technology is a method for sensing an eyeball including: by using an imaging element having an event-driven function, generating a Purkinje detection mode, generating a pupil detection mode, and generating an event-driven mode; and transitioning to the Purkinje detection mode, transitioning to the pupil detection mode, and transitioning to the event-driven mode, and further includes changing to three light emission intensity states using a light emitting device. The three light emission intensities are a high intensity, a medium intensity, and a low intensity, and an intensity difference between the high intensity and the medium intensity is substantially identical to an intensity difference between the medium intensity and the low intensity. Meanwhile, the method for sensing an eyeball in the third embodiment (Example 3 of the method for sensing an eyeball) according to the present technology may be executed using the line-of-sight detection device in the third embodiment (Example 3 of the line-of-sight detection device) according to the present technology.

Then, in the method for sensing an eyeball in the third embodiment (Example 3 of the method for sensing an eyeball) according to the present technology, a transition is made from the Purkinje detection mode to the event-driven mode, a transition is made from the event-driven mode to the Purkinje detection mode, a transition is made from the pupil detection mode to the event-driven mode, a transition is made from the event-driven mode to the pupil detection mode, a transition is made from the Purkinje detection mode to the pupil detection mode, and a transition is made from the pupil detection mode to the Purkinje detection mode.

The line-of-sight detection device and the method for sensing an eyeball in the third embodiment according to the present technology will be described with reference to FIGS. 5A and 5B.

Figure 5A:
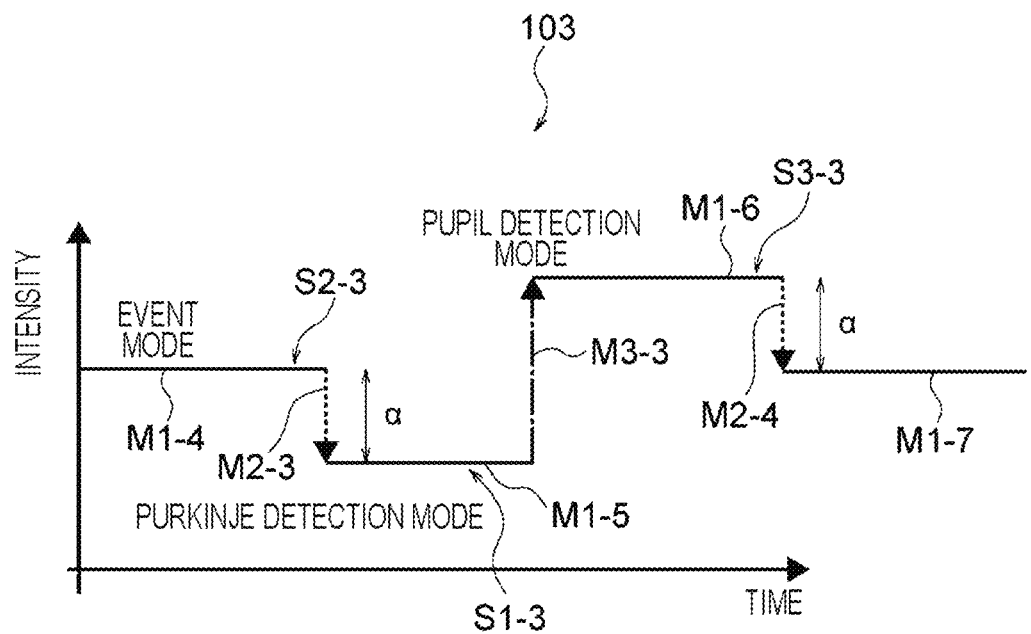
FIGS. 5A and 5B are views illustrating an example of a transition method of three modes (Purkinje detection mode, pupil detection mode, and event-driven mode) in a line-of-sight detection device and a method for sensing an eyeball in a third embodiment to which the present technology is applied.
Figure 5B:
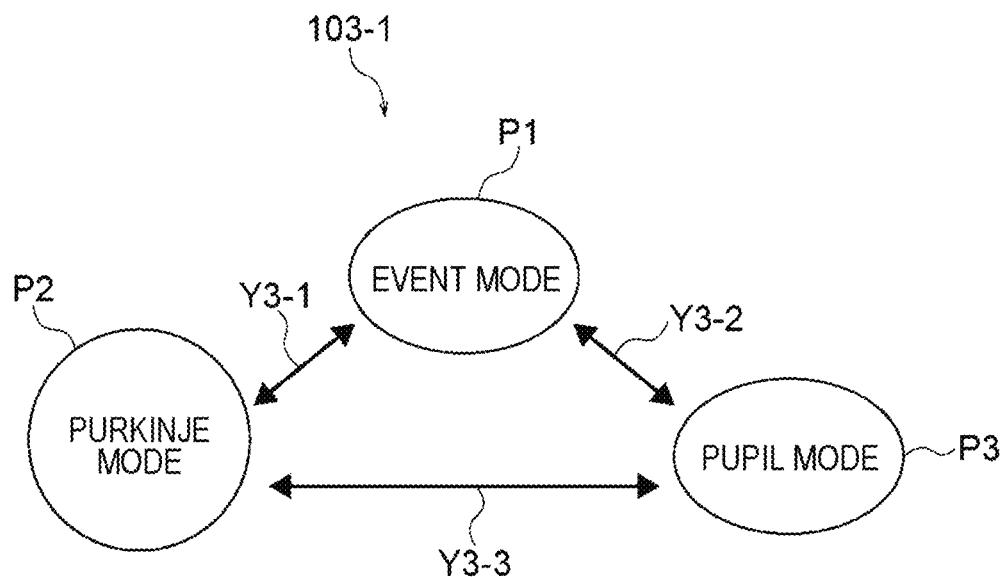

FIGS. 5A and 5B are views illustrating an example of a transition method of three modes (the Purkinje detection mode, the pupil detection mode, and the event-driven mode) in the line-of-sight detection device and the method for sensing an eyeball in the third embodiment according to the present technology. More specifically, FIG. 5A is a view illustrating a transition pattern 103 of the three modes (Purkinje detection mode, pupil detection mode, and event-driven mode). In FIG. 5A, the horizontal axis represents time, and the vertical axis represents a light emission intensity of the light emitting device (for example, an LED). FIG. 5B is a view (also referred to as a state shift diagram 103-1) summarizing a transition relationship (indicated by reference sign 103-1) of the three modes (Purkinje detection mode, pupil detection mode, and event-driven mode).

In the transition pattern 103, a transition is made from an event mode M1-4 in a state where the intensity is constant at a medium intensity S2-3 to a Purkinje mode M2-3 that is a moment when the intensity changes from the medium intensity S2-3 to a low intensity S1-3 (changes with displacement amount of α), subsequently, a transition is made to an event mode M1-5 in a state where the intensity is constant at the low intensity S1-3, and a transition is made to a pupil mode M3-3 that is a moment when the intensity changes from the low intensity S1-3 to a high intensity S3-3 (changes with a displacement amount of 2α). Then, a transition is made from the pupil mode M3-3 to an event mode M1-6 in a state where the intensity is constant at the high intensity S3-3, subsequently, a transition is made to a Purkinje mode M2-4 which is a moment when the intensity changes from the high intensity S3-3 to the medium intensity S2-3 (changes with the displacement amount of α), and a transition is made from the Purkinje mode M2-4 to an event mode M1-7 in a state where the intensity is constant at the medium intensity S2-3.

As described above, the transition pattern 103 has the three intensities, that is, the low intensity S1-3, the medium intensity S2-3, and the high intensity S3-3. The intensity difference (displacement amount) between the low intensity S1-3 and the medium intensity S2-3 is α, and the intensity difference (displacement amount) between the medium intensity S2-3 and the high intensity S3-3 is α. That is, the intensity difference (displacement amount) between the low intensity S1-3 and the medium intensity S2-3 and the intensity difference (displacement amount) between the medium intensity S2-3 and the high intensity S3-3 are the same as a. Then, the intensity difference (displacement amount) between the low intensity S1-3 and the high intensity S3-3 is 2α.

In a section (event mode) in which each intensity (the low intensity S1-3, the medium intensity S2-3, or the high intensity S3-3) is constant, reflected light of the pupil and Purkinje (Fresnel reflection and diffuse reflection components) is triggered with respect to a movement of the eyeball.

At the moment when the displacement transitions from the medium intensity S2-3 to an adjacent intensity (in the Purkinje detection mode (also referred to as Purkinje mode)), the intensity of light is forcibly changed, which is triggered only by a reflective displacement amount of Purkinje light (Fresnel reflection component).

At the moment when a transition is made from the low intensity S1-3 to a different intensity with the displacement of 2α (in the pupil detection mode), the intensity of light is forcibly changed, which is triggered by reflective displacement amounts of reflected light (Fresnel reflection and diffuse reflection components) of the pupil and Purkinje.

As illustrated in the state shift diagram 103-1, in the transition pattern 103, it is possible to transition from the event mode P1 to the Purkinje mode P2, and to transition from the Purkinje mode P2 to the event mode P1 (an arrow Y3-1 illustrated in FIG. 5B). Furthermore, in the transition pattern 103, it is possible to transition from the event mode P1 to the pupil mode P3, and to transition from the pupil mode P3 to the event mode P1 (an arrow Y3-2 illustrated in FIG. 5B). Moreover, in the transition pattern 103, it is possible to transition from the Purkinje mode P2 to the pupil mode P3, and to transition from the pupil mode P3 to the Purkinje mode P2 (an arrow Y3-3 illustrated in FIG. 5B).

Therefore, in the transition pattern 103 (state shift diagram 103-1), the transition from the pupil mode P3 to the Purkinje detection mode P2 is added to the above-described transition pattern 102 (state shift diagram 102-1), and thus, there is one more state transition direction.

As described above, contents that have been described regarding the line-of-sight detection device and the method for sensing an eyeball in the third embodiment (Example 3 of the line-of-sight detection device and Example 3 of the method for sensing an eyeball) according to the present technology can be applied to the line-of-sight detection devices and the methods for sensing an eyeball in the first and second embodiments according to the present technology described above, and the line-of-sight detection devices and the methods for sensing an eyeball in the fourth to tenth embodiments according to the present technology as described later particularly as long as there is no technical contradiction.

5. Fourth Embodiment (Example 4 of Line-of-Sight Detection Device and Example 4 of Method for Sensing Eyeball)

The line-of-sight detection device in the fourth embodiment (Example 4 of the line-of-sight detection device) according to the present technology is a line-of-sight detection device including: an imaging element (for example, a dynamic vision sensor (DVS)) having an event-driven function; a first mode generation unit that generates a Purkinje detection mode; a second mode generation unit that generates a pupil detection mode; and a third mode generation unit that generates an event-driven mode, and further includes a plurality of light emitting devices. In the line-of-sight detection device in the fourth embodiment according to the present technology, the first mode generation unit generates the Purkinje detection mode when each of the plurality of light emitting devices is sequentially turned on.

The method for sensing an eyeball in the fourth embodiment (Example 4 of the method for sensing an eyeball) according to the present technology is a method for sensing an eyeball including: by using an imaging element having an event-driven function, generating a Purkinje detection mode, generating a pupil detection mode, and generating an event-driven mode; and transitioning to the Purkinje detection mode, transitioning to the pupil detection mode, and transitioning to the event-driven mode, and further includes sequentially turning on each of a plurality of light emitting devices using the plurality of light emitting devices to sequentially transition to the Purkinje detection mode. Meanwhile, the method for sensing an eyeball in the fourth embodiment (Example 4 of the method for sensing an eyeball) according to the present technology may be executed using the line-of-sight detection device in the fourth embodiment (Example 4 of the line-of-sight detection device) according to the present technology.

The line-of-sight detection device and the method for sensing an eyeball in the fourth embodiment according to the present technology will be described with reference to FIG. 6.

Figure 6:
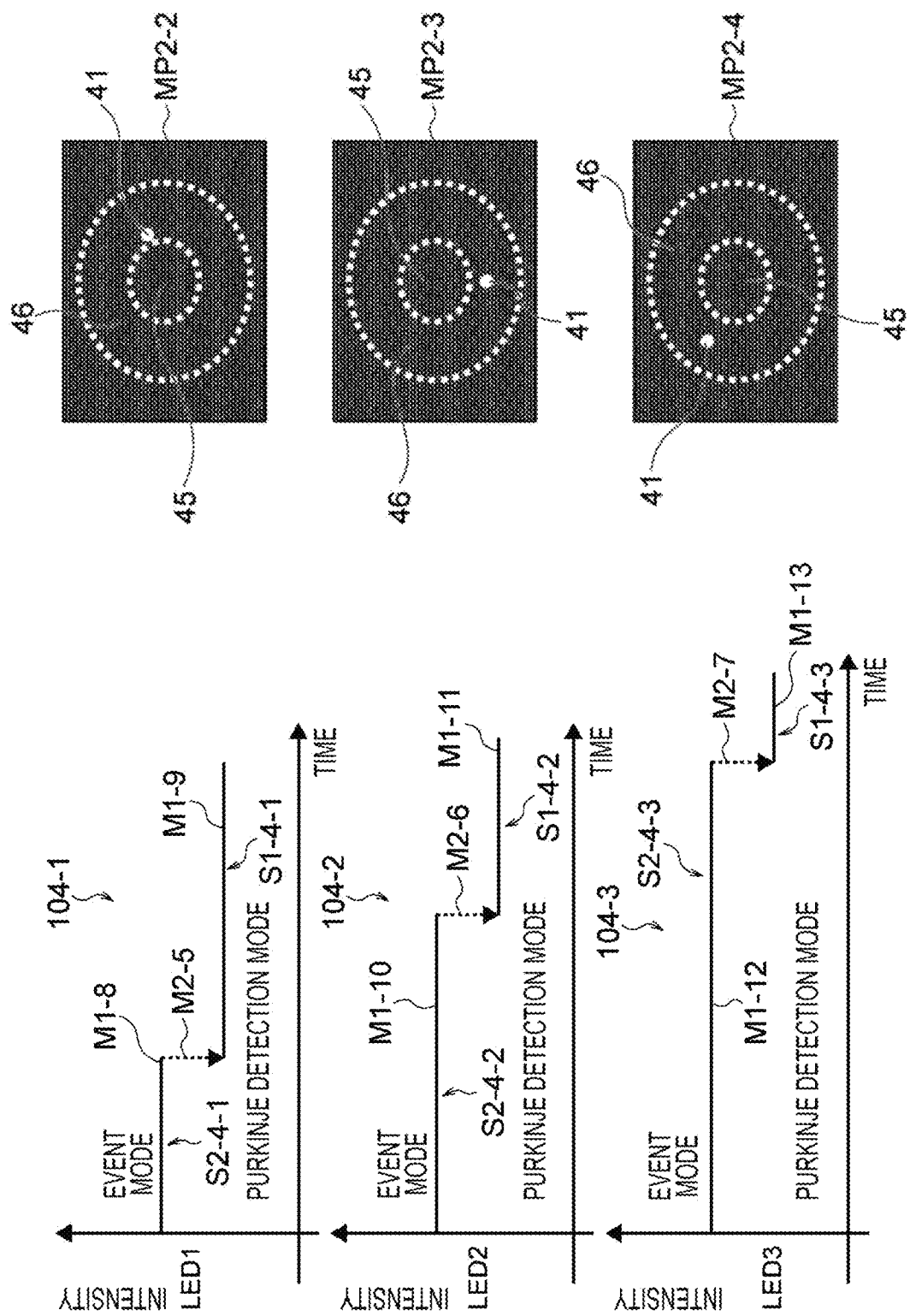
FIG. 6 is a view illustrating an example of a transition method of two modes (event-driven mode and Purkinje detection mode) in a line-of-sight detection device and a method for sensing an eyeball in a fourth embodiment to which the present technology is applied.

FIG. 6 is a view illustrating an example of a transition method of two modes (the event-driven mode and the Purkinje detection mode) in the line-of-sight detection device and the method for sensing an eyeball in the fourth embodiment according to the present technology, and more specifically, illustrates a transition pattern 104-1 of two modes (Purkinje detection mode and event-driven mode), a transition pattern 104-2 of two modes (Purkinje detection mode and event-driven mode), and a transition pattern 104-3 of two modes (Purkinje detection mode and event-driven mode) in order from the upper side of FIG. 6.

A schematic image MP2-2 when the eyeball is sensed in the Purkinje detection mode using the line-of-sight detection device in the fourth embodiment according to the present technology is illustrated on the right side of the transition pattern 104-1 in FIG. 6; a schematic image MP2-3 when the eyeball is sensed in the Purkinje detection mode using the line-of-sight detection device in the fourth embodiment according to the present technology is illustrated on the right side of the transition pattern 104-2 in FIG. 6; and a schematic image MP2-4 when the eyeball is sensed in the Purkinje detection mode using the line-of-sight detection device in the fourth embodiment according to the present technology is illustrated on the right side of the transition pattern 104-3 in FIG. 6.

An LED 1 is used as the light emitting device. In the transition pattern 104-1, a transition is made from an event mode M1-8 in a state where the intensity is constant at a high intensity S2-4-1 to a Purkinje detection mode M2-5 that is a moment when the intensity changes from the high intensity S2-4-1 to a low intensity S1-4-1, and subsequently, a transition is made from the Purkinje detection mode M2-5 to an event mode M1-9 in a state where the intensity is constant at the low intensity S1-4-1. Note that the LED 1 can also have an intensity higher than the high intensity S2-4-1 or an intensity lower than the low intensity S1-4-1, that is, can have a total of three intensities together with the high intensity S2-4-1 and the low intensity S1-4-1. Note that the LED 1 may have a total of four or more intensities.

An LED 2 is used as the light emitting device. In the transition pattern 104-2, a transition is made from an event mode M1-10 in a state where the intensity is constant at a high intensity S2-4-2 to a Purkinje detection mode M2-6 that is a moment when the intensity changes from the high intensity S2-4-2 to a low intensity S1-4-2, and subsequently, a transition is made from the Purkinje detection mode M2-6 to an event mode M1-11 in a state where the intensity is constant at the low intensity S1-4-2. Note that the LED 2 can also have an intensity higher than the high intensity S2-4-2 or an intensity lower than the low intensity S1-4-2, that is, can have a total of three intensities together with the high intensity S2-4-2 and the low intensity S1-4-2. Note that the LED 2 may have a total of four or more intensities.

An LED 3 is used as the light emitting device. In the transition pattern 104-3, a transition is made from an event mode M1-12 in a state where the intensity is constant at a high intensity S2-4-3 to a Purkinje detection mode M2-7 that is a moment when the intensity changes from the high intensity S2-4-3 to a low intensity S1-4-3, and subsequently, a transition is made from the Purkinje detection mode M2-7 to an event mode M1-13 in a state where the intensity is constant at the low intensity S1-4-3. Note that the LED 3 can also have an intensity higher than the high intensity S2-4-3 or an intensity lower than the low intensity S1-4-3, that is, can have a total of three intensities together with the high intensity S2-4-3 and the low intensity S1-4-3. Note that the LED 2 may have a total of four or more intensities.

As described above, when the transitions are sequentially made from the event mode M1-8, the event mode M1-10, and the event mode M1-12 to the Purkinje detection mode M2-5, the Purkinje detection mode M2-6, and the Purkinje detection mode M2-7, respectively, with a lapse of time (transitions are sequentially made to light emission timings of the respective LEDs 1 to 3 with a lapse of time), the Purkinje image 41 located at the upper right of the pupil 45 can be detected in the image MP2-2, the Purkinje image 41 located below the pupil 45 can be detected in the image MP2-3, and the Purkinje image 41 located at the upper left of the pupil 45 can be detected in the image MP2-4, and the accuracy of labeling can be improved. Then, for example, in a case where the line-of-sight detection device in the fourth embodiment according to the present technology constitutes a glasses-type display device, the LED 1 is arranged on the upper right of a rim portion forming a front portion of a frame, the LED 2 is arranged below the rim portion forming the front portion of the frame, and the LED 3 is arranged at the upper left of the rim portion forming the front portion of the frame when viewed from the outside of the frame (when a wearer wearing the glasses-type display device is viewed).

Note that the three LEDs (LEDs 1 to 3) have been described, but the number of LEDs (for example, the number of LEDs may be two or four or more) is not limited as long as the accuracy of labeling can be improved.

As described above, contents that have been described regarding the line-of-sight detection device and the method for sensing an eyeball in the fourth embodiment (Example 4 of the line-of-sight detection device and Example 4 of the method for sensing an eyeball) according to the present technology can be applied to the line-of-sight detection devices and the methods for sensing an eyeball in the first to third embodiments according to the present technology described above, and the line-of-sight detection devices and the methods for sensing an eyeball in the fifth to tenth embodiments according to the present technology as described later particularly as long as there is no technical contradiction.

6. Fifth Embodiment (Example 5 of Line-of-Sight Detection Device and Example 5 of Method for Sensing Eyeball)

The line-of-sight detection device in the fifth embodiment (Example 5 of the line-of-sight detection device) according to the present technology is a line-of-sight detection device including: an imaging element (for example, a dynamic vision sensor (DVS)) having an event-driven function; a first mode generation unit that generates a Purkinje detection mode; a second mode generation unit that generates a pupil detection mode; and a third mode generation unit that generates an event-driven mode, and further includes a plurality of light emitting devices. In the line-of-sight detection device in the fifth embodiment according to the present technology, the second mode generation unit generates the pupil detection mode when the plurality of light emitting devices changes light emission intensities substantially simultaneously.

The method for sensing an eyeball in the fifth embodiment (Example 5 of the method for sensing an eyeball) according to the present technology is a method for sensing an eyeball including: by using an imaging element having an event-driven function, generating a Purkinje detection mode, generating a pupil detection mode, and generating an event-driven mode; and transitioning to the Purkinje detection mode, transitioning to the pupil detection mode, and transitioning to the event-driven mode, and further includes substantially simultaneously changing light emission intensities of a plurality of light emitting devices using the plurality of light emitting devices to transition to the pupil detection mode. Meanwhile, the method for sensing an eyeball in the fifth embodiment (Example 5 of the method for sensing an eyeball) according to the present technology may be executed using the line-of-sight detection device in the fifth embodiment (Example 5 of the line-of-sight detection device) according to the present technology.

The line-of-sight detection device and the method for sensing an eyeball in the fifth embodiment according to the present technology will be described with reference to FIG. 7.

Figure 7:
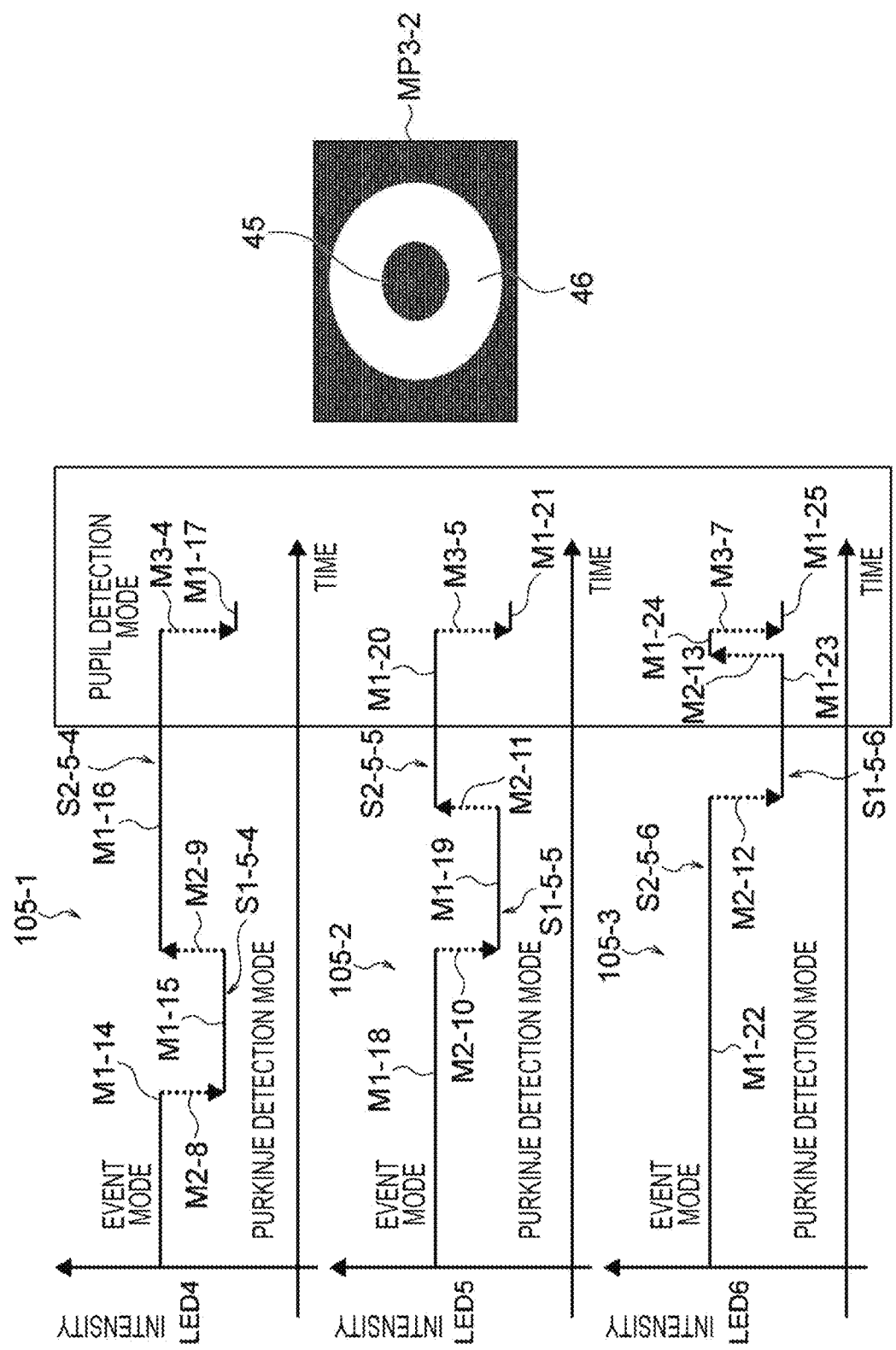
FIG. 7 is a view illustrating an example of a transition method of three modes (event-driven mode, Purkinje detection mode, and pupil detection mode) in a line-of-sight detection device and a method for sensing an eyeball in a fifth embodiment to which the present technology is applied.

FIG. 7 is a view illustrating an example of a transition method of three modes (the event-driven mode, the Purkinje detection mode, and the pupil detection mode) in the line-of-sight detection device and the method for sensing an eyeball in the fifth embodiment according to the present technology, and more specifically, illustrates a transition pattern 105-1 of three modes (event-driven mode, Purkinje detection mode, and pupil detection mode), a transition pattern 105-2 of three modes (event-driven mode, Purkinje detection mode, and pupil detection mode), and a transition pattern 105-3 of three modes (event-driven mode, Purkinje detection mode, and pupil detection mode) in order from the upper side of FIG. 7.

On the right side of the transition patterns 105-1, 105-2, and 105-3 in FIG. 7, a schematic image MP3-2 when the eyeball is sensed in the pupil detection mode using the line-of-sight detection device in the fifth embodiment according to the present technology is illustrated.

An LED 4 is used as the light emitting device. In the transition pattern 105-1, a transition is made from an event mode M1-14 in a state where the intensity is constant at a high intensity S2-5-4 to a Purkinje detection mode M2-8 that is a moment when the intensity changes from the high intensity S2-5-4 to a low intensity S1-5-4, and subsequently, a transition is made from the Purkinje detection mode M2-8 to an event mode M1-15 in a state where the intensity is constant at the low intensity S1-5-4. Next, a transition is made from the event mode M1-15 to a Purkinje detection mode M2-9 that is a moment when the intensity changes from the low intensity S1-5-4 to the high intensity S2-5-4, and subsequently, a transition is made to an event mode M1-16 in a state where the intensity is constant at the high intensity S2-5-4. A transition is made from the event mode M1-16 to a Purkinje detection mode M3-4 that is a moment when the intensity changes from the high intensity S2-5-4 to the low intensity S1-5-4, and a transition is made from the Purkinje detection mode M3-4 to an event mode M1-17 in a state where the intensity is constant at the low intensity S1-5-4.

An LED 5 is used as the light emitting device. In the transition pattern 105-2, a transition is made from an event mode M1-18 in a state where the intensity is constant at a high intensity S2-5-5 to a Purkinje detection mode M2-10 that is a moment when the intensity changes from the high intensity S2-5-5 to a low intensity S1-5-5, and subsequently, a transition is made from the Purkinje detection mode M2-10 to an event mode M1-19 in a state where the intensity is constant at the low intensity S1-5-5. Next, a transition is made from the event mode M1-19 to a Purkinje detection mode M2-11 that is a moment when the intensity changes from the low intensity S1-5-5 to the high intensity S2-5-5, and subsequently, a transition is made to an event mode M1-20 in a state where the intensity is constant at the high intensity S2-5-5. A transition is made from the event mode M1-20 to a Purkinje detection mode M3-5 that is a moment when the intensity changes from the high intensity S2-5-5 to the low intensity S1-5-5, and a transition is made from the Purkinje detection mode M3-5 to an event mode M1-21 in a state where the intensity is constant at the low intensity S1-5-5.

An LED 6 is used as the light emitting device. In the transition pattern 105-3, a transition is made from an event mode M1-22 in a state where the intensity is constant at a high intensity S2-5-6 to a Purkinje detection mode M2-12 that is a moment when the intensity changes from the high intensity S2-5-6 to a low intensity S1-5-6, and subsequently, a transition is made from the Purkinje detection mode M2-12 to an event mode M1-23 in a state where the intensity is constant at the low intensity S1-5-6. Next, a transition is made from the event mode M1-23 to a Purkinje detection mode M2-13 that is a moment when the intensity changes from the low intensity S1-5-6 to the high intensity S2-5-6, and subsequently, a transition is made to an event mode M1-24 in a state where the intensity is constant at the high intensity S2-5-6. A transition is made from the event mode M1-24 to a Purkinje detection mode M3-7 that is a moment when the intensity changes from the high intensity S2-5-6 to the low intensity S1-5-6, and a transition is made from the Purkinje detection mode M3-7 to an event mode M1-25 in a state where the intensity is constant at the low intensity S1-5-6.

As described above, the pupil detection mode is generated when the three LEDs (LED 4 to LED 6) are simultaneously turned on to change the intensities and to simultaneously transition to the three Purkinje detection modes M3-4, M3-5, and M3-6, respectively, in the respective transition patterns 105-1, 105-2, and 105-3, and as a result, a transition is made to the pupil detection mode.

For example, when an intensity difference (displacement amount) between the high intensity S2-5-4 and the low intensity S1-5-4 is α, an intensity difference (displacement amount) between the high intensity S2-5-5 and the low intensity S1-5-5 is α, and an intensity difference (displacement amount) between the high intensity S2-5-6 and the low intensity S1-5-6 is α, the intensity changes by 3a in total so that the transition is made to the pupil detection mode. Note that it is possible to transition to the pupil detection mode if the intensity changes by 2α or more.

Note that the three LEDs (LEDs 4 to 6) have been described, but the number of LEDs (for example, the number of LEDs may be two or four or more) is not limited as long as, for example, a plurality of the LEDs is simultaneously turned on, the intensity changes by 2α or more, and the transition to the pupil detection mode is possible.

As described above, contents that have been described regarding the line-of-sight detection device and the method for sensing an eyeball in the fifth embodiment (Example 5 of the line-of-sight detection device and Example 5 of the method for sensing an eyeball) according to the present technology can be applied to the line-of-sight detection devices and the methods for sensing an eyeball in the first to fourth embodiments according to the present technology described above, and the line-of-sight detection devices and the methods for sensing an eyeball in the sixth to tenth embodiments according to the present technology as described later particularly as long as there is no technical contradiction.

7. Sixth Embodiment (Example 6 of Line-of-Sight Detection Device and Example 6 of Method for Sensing Eyeball)

The line-of-sight detection device in the sixth embodiment (Example 6 of the line-of-sight detection device) according to the present technology is a line-of-sight detection device including: an imaging element (for example, a dynamic vision sensor (DVS)) having an event-driven function; a first mode generation unit that generates a Purkinje detection mode; a second mode generation unit that generates a pupil detection mode; and a third mode generation unit that generates an event-driven mode, and further includes a light emitting device. In the line-of-sight detection device in the sixth embodiment (Example 6 of the line-of-sight detection device) according to the present technology, a signal is acquired in synchronization with a time stamp of a change in a light emission intensity of the light emitting device in the Purkinje detection mode and the pupil detection mode, and a signal is acquired by performing time stamp accumulation in the event-driven mode.

The method for sensing an eyeball in the sixth embodiment (Example 6 of the method for sensing an eyeball) according to the present technology is a method for sensing an eyeball including: by using an imaging element having an event-driven function, generating a Purkinje detection mode, generating a pupil detection mode, and generating an event-driven mode; and transitioning to the Purkinje detection mode, transitioning to the pupil detection mode, and transitioning to the event-driven mode, and further includes: acquiring a signal in synchronization with a time stamp of a change in a light emission intensity of a light emitting device in the Purkinje detection mode and the pupil detection mode; and performing time stamp accumulation to acquire a signal in the event-driven mode. Meanwhile, the method for sensing an eyeball in the sixth embodiment (Example 6 of the method for sensing an eyeball) according to the present technology may be executed using the line-of-sight detection device in the sixth embodiment (Example 6 of the line-of-sight detection device) according to the present technology.

The line-of-sight detection device and the method for sensing an eyeball in the sixth embodiment according to the present technology will be described with reference to FIG. 8.

Figure 8:
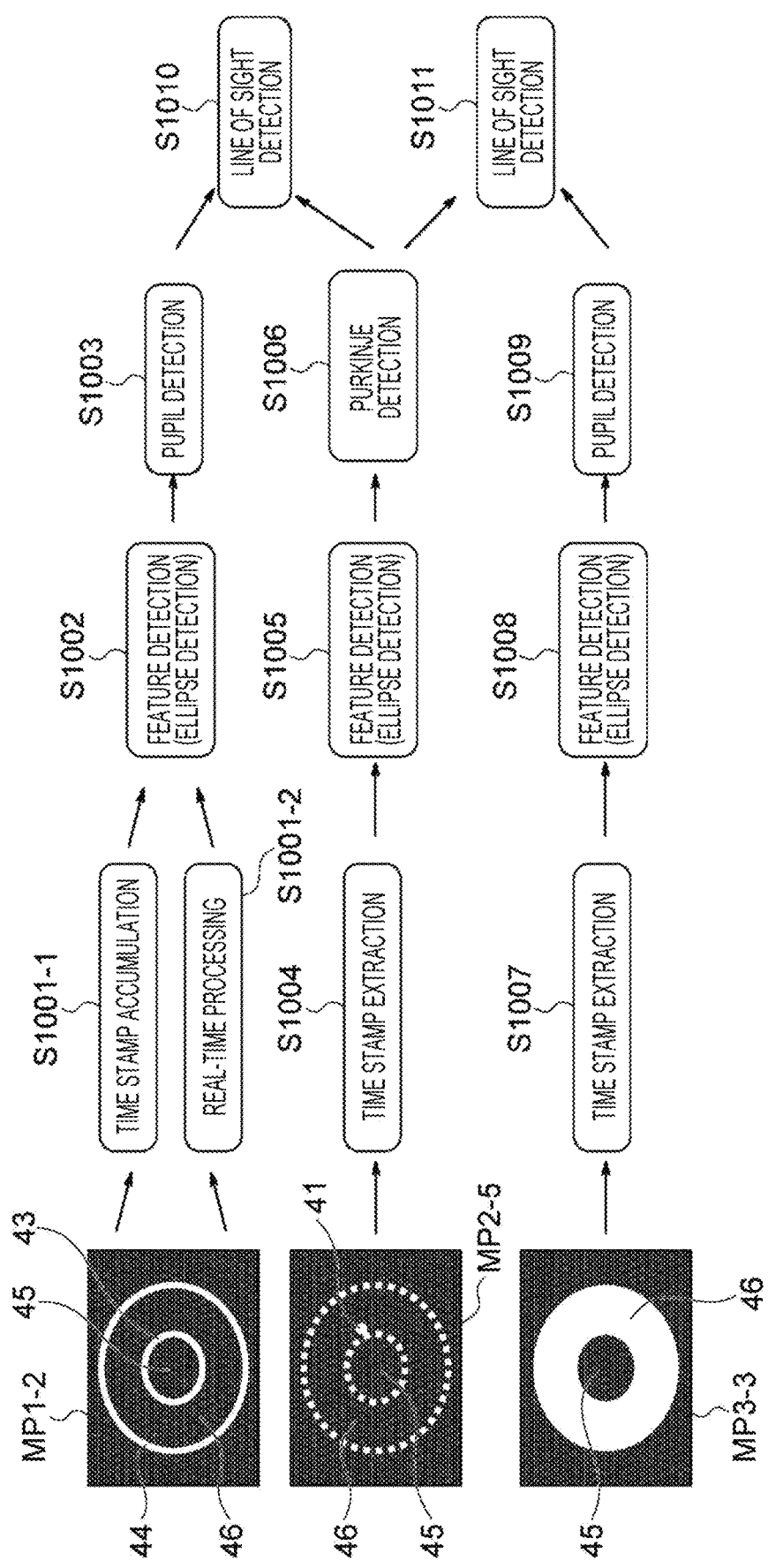
FIG. 8 is a view illustrating an example of a detection method in three modes (event-driven mode, Purkinje detection mode, and pupil detection mode) in a line-of-sight detection device and a method for sensing an eyeball in a sixth embodiment to which the present technology is applied.

FIG. 8 is a view illustrating an example of a detection method in three modes (the event-driven mode, the Purkinje detection mode, and the pupil detection mode) in the line-of-sight detection device and the method for sensing an eyeball in the sixth embodiment according to the present technology. On the left side of FIG. 8, a schematic image MP1-2 when the eyeball is sensed in the event-driven mode using the line-of-sight detection device in the sixth embodiment according to the present technology, a schematic image MP2-5 when the eyeball is sensed in the Purkinje detection mode, and a schematic image MP3-3 when the eyeball is sensed in the pupil detection mode are illustrated in order from the upper side of FIG. 8.

A pupil is detected in the event-driven mode, Purkinje is detected in the Purkinje detection mode, and a pupil is detected in the pupil detection mode. Line-of-sight detection is performed using the pupil detection in the event-driven mode and the Purkinje detection in the Purkinje detection mode. The line-of-sight detection is performed using the pupil detection in the pupil detection mode and the Purkinje detection in the Purkinje detection mode.

In the event-driven mode (the image MP1-2), a time stamp is accumulated in step S1000-1 as a method of acquiring a signal and performing signal processing. The time stamp is accumulated to acquire a signal (by a signal acquisition unit). Feature detection is performed by frame processing in step S1002, and pupil detection is performed in step S1003. Alternatively, in the event-driven mode, real-time processing is performed in step S1001-2, feature detection is performed in step S1002, and pupil detection is performed in step S1003. For the feature detection in step S1002, for example, ellipse detection or a neural network such as a DNN or an RNN is used.

In the Purkinje detection mode (the image MP2-5), time stamp extraction is performed in synchronization with a change in an LED in step S1004 as a method of acquiring a signal and performing signal processing. A signal is acquired in synchronization with a time stamp of an intensity change (by the signal acquisition unit). The same feature detection as described above is performed using event data between the obtained time stamps in step S1005, and Purkinje detection is performed in step S1006.

In the pupil detection mode (the image MP3-3), time stamp extraction is performed in synchronization with a change in the LED in step S1007 as a method of acquiring a signal and performing signal processing. A signal is acquired in synchronization with a time stamp of an intensity change (by the signal acquisition unit). The same feature detection as described above is performed on event data between the obtained time stamps in step S1008, and pupil detection is performed in step S1009.

Line-of-sight detection is performed in step S1010 using the pupil detection in step S1003 and the Purkinje detection in step 1006.

Line-of-sight detection is performed in step S1011 using the pupil detection in step S1009 and the Purkinje detection in step 1006.

As described above, contents that have been described regarding the line-of-sight detection device and the method for sensing an eyeball in the sixth embodiment (Example 6 of the line-of-sight detection device and Example 6 of the method for sensing an eyeball) according to the present technology can be applied to the line-of-sight detection devices and the methods for sensing an eyeball in the first to fifth embodiments according to the present technology described above, and the line-of-sight detection devices and the methods for sensing an eyeball in the seventh to tenth embodiments according to the present technology as described later particularly as long as there is no technical contradiction.

8. Seventh Embodiment (Example 7 of Line-of-Sight Detection Device and Example 7 of Method for Sensing Eyeball)

The line-of-sight detection device in the seventh embodiment (Example 7 of the line-of-sight detection device) according to the present technology is a line-of-sight detection device including: an imaging element (for example, a dynamic vision sensor (DVS)) having an event-driven function; a first mode generation unit that generates a Purkinje detection mode; a second mode generation unit that generates a pupil detection mode; and a third mode generation unit that generates an event-driven mode. In the line-of-sight detection device of the seventh embodiment (Example 7 of the line-of-sight detection device) according to the present technology, the second mode generation unit generates the pupil detection mode when detection is lost in the event-driven mode or when a detection likelihood of the event-driven mode is lower than a predetermined value (reference value).

The method for sensing an eyeball in the seventh embodiment (Example 7 of the method for sensing an eyeball) according to the present technology is a method for sensing an eyeball including: by using an imaging element having an event-driven function, generating a Purkinje detection mode, generating a pupil detection mode, and generating an event-driven mode; and transitioning to the Purkinje detection mode, transitioning to the pupil detection mode, and transitioning to the event-driven mode, and further includes transitioning to the pupil detection mode when detection is lost in the event-driven mode or when a detection likelihood of the event-driven mode is lower than a predetermined value. Meanwhile, the method for sensing an eyeball in the seventh embodiment (Example 7 of the method for sensing an eyeball) according to the present technology may be executed using the line-of-sight detection device in the seventh embodiment (Example 7 of the line-of-sight detection device) according to the present technology.

The line-of-sight detection device and the method for sensing an eyeball in the seventh embodiment according to the present technology will be described with reference to FIGS. 9, 10A, 10B, 10C, and 10D.

Figure 9:
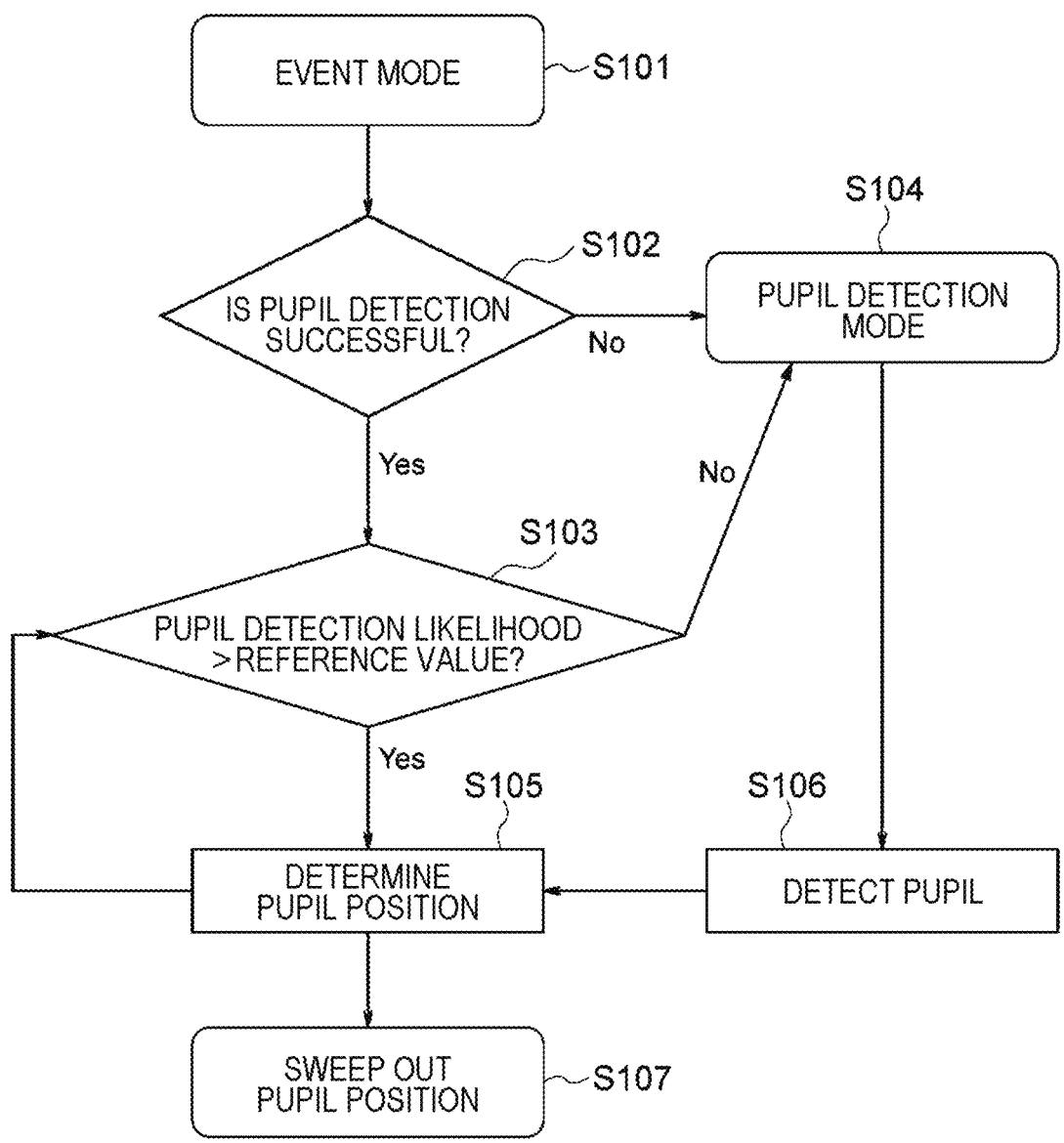
FIG. 9 is a view illustrating an example of a pupil detection flow in a line-of-sight detection device and a method for sensing an eyeball in a seventh embodiment to which the present technology is applied.

FIG. 9 is a view illustrating an example of a pupil detection flow in the line-of-sight detection device and the method for sensing an eyeball in the seventh embodiment according to the present technology.

In step S101 in FIG. 9, a transition is made to an event mode (the event-driven mode) (the event mode (event-driven mode) is generated).

Pupil detection is performed in step S102, and the flow proceeds to step S103 in a case where the pupil detection is successful (Yes), or proceeds to step 104 in a case where the pupil detection has failed (No).

In step S103 (in the case where the pupil detection is successful (Yes)), it is determined whether or not a pupil detection likelihood is greater than a reference value. The flow proceeds to step S105 in a case where the pupil detection likelihood is greater than the reference value (Yes), or proceeds to step S104 in a case where the pupil detection likelihood is not greater than the reference value (No).

In step S105 (in the case where the pupil detection likelihood is greater than the reference value (Yes)), a pupil position is determined. If necessary, the flow returns to step S103, and it is determined again whether or not the pupil detection likelihood is greater than the reference value. In a case where the flow does not return to step S103, the pupil position is swept out in step S107.

As described above, in the case where the pupil detection has failed (No), the flow proceeds to step 104, and the pupil detection mode is generated in step 104 (a transition is made to the pupil detection mode). Next, pupil detection is performed in step S106. Next, a pupil position is determined in step S105. If necessary, the flow proceeds to step S103, and it is determined whether or not the pupil detection likelihood is greater than the reference value. In a case where the flow does not return to step S103, sweep-out of the pupil position is performed in step S107.

As described above, in the case where the pupil detection likelihood is not greater than the reference value (No), the flow proceeds to step 104, and the pupil detection mode is generated in step 104 (the transition is made to the pupil detection mode). Next, pupil detection is performed in step S106. Next, a pupil position is determined in step S105. If necessary, the flow proceeds to step S103, and it is determined whether or not the pupil detection likelihood is greater than the reference value. In a case where the flow does not return to step S103, sweep-out of the pupil position is performed in step S107.

In the case where the pupil detection likelihood is not greater than the reference value (No), a loop of step S104 (pupil detection mode)→step S106 (pupil detection)→step S105 (pupil position determination)→step S103 (determination on whether or not the pupil detection likelihood is greater than the reference value)→step 104 (pupil detection mode) is repeated.

As described above, the transition is made to the pupil detection mode (the pupil detection mode is generated) when the determination of the pupil position in the event mode fails. As a result, the transition to the pupil detection mode (the generation of the pupil detection mode) is suppressed to a necessary minimum, and it is possible to reduce power consumption and to increase the speed of the pupil detection and the like.

Figure 10:
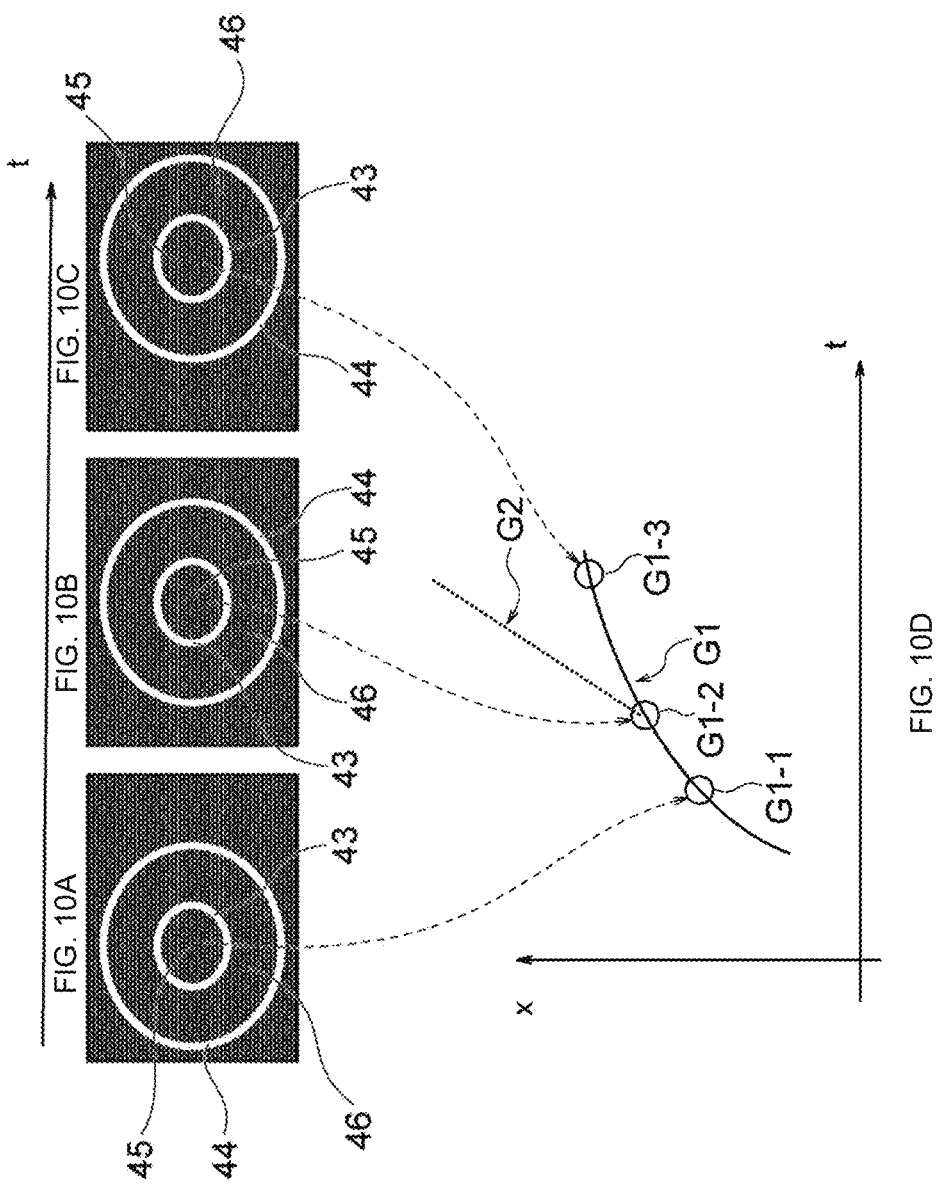
FIGS. 10A, 10B, 10C, and 10D are views for describing determination of a position of a pupil using an optical flow for likelihood estimation in the line-of-sight detection device and the method for sensing an eyeball in the seventh embodiment to which the present technology is applied.

FIGS. 10A, 10B, 10C, and 10D are views for describing determination of a position of a pupil using an optical flow for likelihood estimation in the line-of-sight detection device and the method for sensing an eyeball in the seventh embodiment according to the present technology. More specifically, images illustrated in FIGS. 10A, 10B, and 10C are schematic views when the eyeball is sensed in the event-driven mode. As time (t) passes (as FIGS. 10A, 10B, and 10C proceed in this order), the pupil 45 illustrated in FIGS. 10A, 10B, and 10C is shifted from a left position of the image (FIG. 10A) to a center position (FIG. 10B), and then, shifted from the center position (FIG. 10B) to a right position (FIG. 10C).

In a graph illustrated in FIG. 10D, the horizontal axis is the time (t) and the vertical axis is a position (x) of the pupil. A line G1 illustrated in FIG. 10D is a curve indicating a likely shift of the pupil 45, and a line G2 is a line indicating a detection error of the pupil 45. The position of the pupil 45 illustrated in FIG. 10A corresponds to a circular region G1-1 on the line G1, the position of the pupil 45 illustrated in FIG. 10B corresponds to a circular region G1-2 on the line G1, and the position of the pupil 45 illustrated in FIG. 10C corresponds to a circular region G1-3 on the line G1. That is, it can be confirmed that the shifts of the pupil 45 illustrated in FIGS. 10A, 10B, and 10C correspond to the likely shift.

As described above, the optical flow can be used for the likelihood estimation. For example, during a saccade period or the like, a pupil shift in the time-axis direction draws a likely curve (for example, the line G1 in FIG. 10D). Those deviating from the shift are identified as detection errors (for example, the line G2 in FIG. 10D). Then, the graph illustrated in FIG. 10D can be used in step S103 (determination on whether or not the pupil detection likelihood is greater than the reference value) illustrated in FIG. 9 described above.

As described above, contents that have been described regarding the line-of-sight detection device and the method for sensing an eyeball in the seventh embodiment (Example 7 of the line-of-sight detection device and Example 7 of the method for sensing an eyeball) according to the present technology can be applied to the line-of-sight detection devices and the methods for sensing an eyeball in the first to sixth embodiments according to the present technology described above, and the line-of-sight detection devices and the methods for sensing an eyeball in the eighth to tenth embodiments according to the present technology as described later particularly as long as there is no technical contradiction.

9. Eighth Embodiment (Example 8 of Line-of-Sight Detection Device and Example 8 of Method for Sensing Eyeball)

The line-of-sight detection device in the eighth embodiment (Example 8 of the line-of-sight detection device) according to the present technology is a line-of-sight detection device including: an imaging element (for example, a dynamic vision sensor (DVS)) having an event-driven function; a first mode generation unit that generates a Purkinje detection mode; a second mode generation unit that generates a pupil detection mode; and a third mode generation unit that generates an event-driven mode. In the line-of-sight detection device of the eighth embodiment (Example 8 of the line-of-sight detection device) according to the present technology, the second mode generation unit generates the pupil detection mode when an end of a saccade is detected in the event-driven mode.

The method for sensing an eyeball in the eighth embodiment (Example 8 of the method for sensing an eyeball) according to the present technology is a method for sensing an eyeball including: by using an imaging element having an event-driven function, generating a Purkinje detection mode, generating a pupil detection mode, and generating an event-driven mode; and transitioning to the Purkinje detection mode, transitioning to the pupil detection mode, and transitioning to the event-driven mode, and further includes transitioning to the pupil detection mode when an end of a saccade is detected in the event-driven mode. Meanwhile, the method for sensing an eyeball in the eighth embodiment (Example 8 of the method for sensing an eyeball) according to the present technology may be executed using the line-of-sight detection device in the eighth embodiment (Example 8 of the line-of-sight detection device) according to the present technology.

The line-of-sight detection device and the method for sensing an eyeball in the eighth embodiment according to the present technology will be described with reference to FIG. 11.

Figure 11:
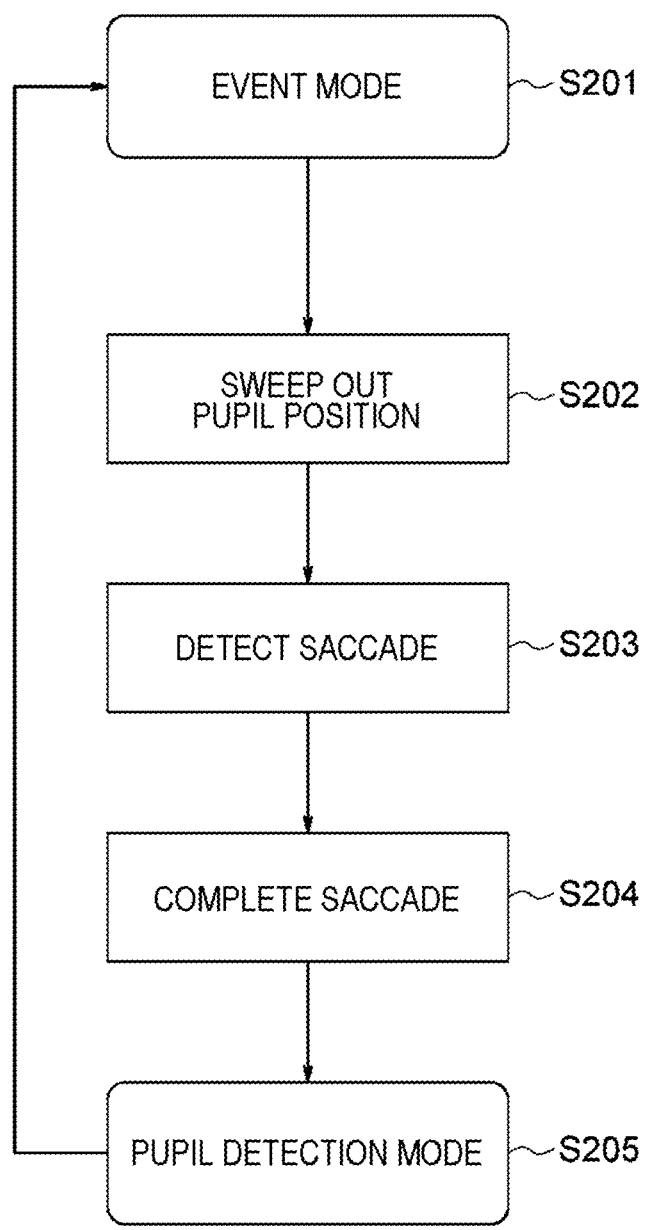
FIG. 11 is a view illustrating an example of a pupil detection flow in a line-of-sight detection device and a method for sensing an eyeball in an eighth embodiment to which the present technology is applied.

FIG. 11 is a view illustrating an example of a pupil detection flow in the line-of-sight detection device and the method for sensing an eyeball in the eighth embodiment according to the present technology.

In step S201 in FIG. 11, a transition is made to an event mode (the event-driven mode). (The event mode (event-driven mode) is generated).

In step S202, a pupil position is swept out.

Saccade detection is performed in step S203, and a saccade is completed in step S204.

After the completion of the saccade, a transition is made to the pupil detection mode in step S205 (the pupil detection mode is generated).

A transition can be made from the pupil detection mode in step S205 to the event mode (event-driven mode) (the event mode (event-driven mode) can be generated) (step S201).

Since the transition is made to the pupil detection mode (step S205) at the timing when the saccade is completed (step S204) from a result of the pupil detection in the event mode, the detection accuracy can be improved with the minimum latency.

As described above, contents that have been described regarding the line-of-sight detection device and the method for sensing an eyeball in the eighth embodiment (Example 8 of the line-of-sight detection device and Example 8 of the method for sensing an eyeball) according to the present technology can be applied to the line-of-sight detection devices and the methods for sensing an eyeball in the first to seventh embodiments according to the present technology described above, and the line-of-sight detection devices and the methods for sensing an eyeball in the ninth and tenth embodiments according to the present technology as described later particularly as long as there is no technical contradiction.

10. Ninth Embodiment (Example 9 of Line-of-Sight Detection Device and Example 9 of Method for Sensing Eyeball)

The line-of-sight detection device in the ninth embodiment (Example 9 of the line-of-sight detection device) according to the present technology is a line-of-sight detection device including: an imaging element (for example, a dynamic vision sensor (DVS)) having an event-driven function; a first mode generation unit that generates a Purkinje detection mode; a second mode generation unit that generates a pupil detection mode; and a third mode generation unit that generates an event-driven mode, and further includes a light emitting device. The imaging element having the event-driven function provided in the line-of-sight detection device in the ninth embodiment according to the present technology includes a first pixel and a second pixel which have different thresholds. The first pixel and the second pixel are arranged in a Bayer array. The arrangement in the Bayer array refers to, for example, an arrangement of the first pixels and the second pixels in a matrix in which the first pixels and the second pixels are alternately arranged in each of a row direction and a column direction. Then, the light emitting device provided in the line-of-sight detection device in the ninth embodiment according to the present technology has two light emission intensities.

The method for sensing an eyeball in the ninth embodiment (Example 9 of the method for sensing an eyeball) according to the present technology is a method for sensing an eyeball including: by using an imaging element having an event-driven function, generating a Purkinje detection mode, generating a pupil detection mode, and generating an event-driven mode; and transitioning to the Purkinje detection mode, transitioning to the pupil detection mode, and transitioning to the event-driven mode, and further includes changing to two light emission intensity states using a light emitting device. The imaging element having the event-driven function used in the method for sensing an eyeball in the ninth embodiment according to the present technology includes a first pixel and a second pixel which have different thresholds. The first pixel and the second pixel are arranged in a Bayer array. The arrangement in the Bayer array refers to, for example, an arrangement of the first pixels and the second pixels in a matrix in which the first pixels and the second pixels are alternately arranged in each of a row direction and a column direction. Meanwhile, the method for sensing an eyeball in the ninth embodiment (Example 9 of the method for sensing an eyeball) according to the present technology may be executed using the line-of-sight detection device in the ninth embodiment (Example 9 of the line-of-sight detection device) according to the present technology.

The line-of-sight detection device and the method for sensing an eyeball in the ninth embodiment according to the present technology will be described with reference to FIGS. 12A and 12B.

Figure 12:
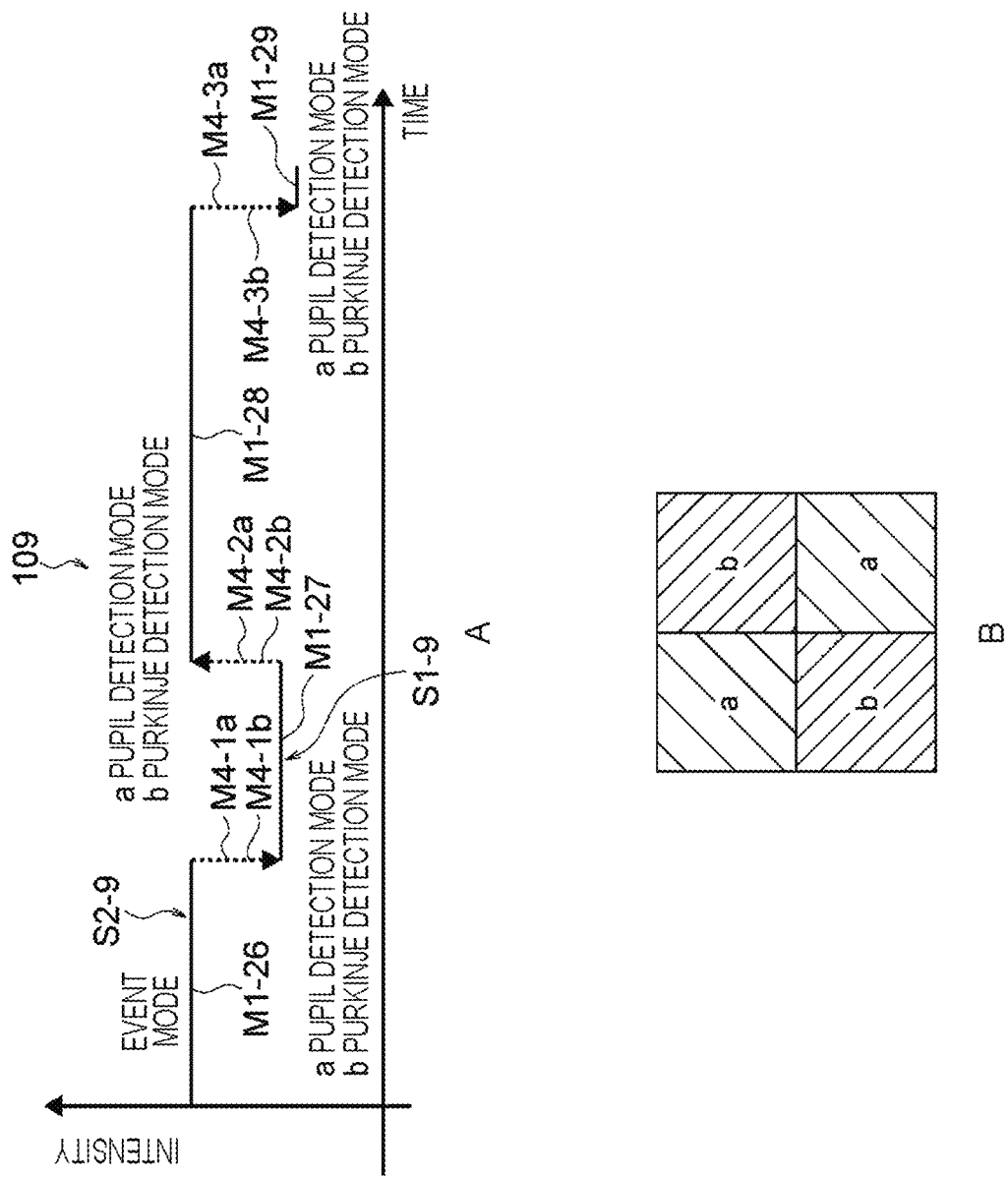
FIGS. 12A and 12B are views illustrating an example of a transition method of three modes (event-driven mode, Purkinje detection mode, and pupil detection mode) in a line-of-sight detection device and a method for sensing an eyeball in a ninth embodiment to which the present technology is applied.

FIGS. 12A and 12B are views illustrating an example of a transition method of three modes (the event-driven mode, the Purkinje detection mode, and the pupil detection mode) in the line-of-sight detection device and the method for sensing an eyeball in the ninth embodiment according to the present technology. More specifically, FIG. 12A is a view illustrating a transition pattern 109 of the three modes (Purkinje detection mode, pupil detection mode, and event-driven mode). FIG. 12B is a view illustrating a configuration example of pixels included in the imaging element having the event-driven function provided in the line-of-sight detection device in the ninth embodiment according to the present technology, and more specifically, illustrates pixels a (the first pixels) and pixels b (the second pixels) are arranged in a Bayer array. That is, the pixels a and the pixels b are arranged in a matrix, and the pixels a and the pixels b are alternately arranged in each of a row direction (left-right direction in FIG. 12B) and a column direction (up-down direction in FIG. 12B).

In a transition pattern 109, a transition is made from an event mode M1-26 in a state where the intensity is constant at a high intensity S2-9 to a pupil detection mode M4-1a in the pixel a and to a Purkinje detection mode M4-1b in the pixel b at a moment when the intensity changes from the high intensity S2-9 to a low intensity S1-9, and subsequently, a transition is made from the pupil detection mode M4-1a and the Purkinje detection mode M4-1b to an event mode M1-27 in a state where the intensity is constant at the low intensity S1-9. Next, a transition is made from the event mode M1-27 to a pupil detection mode M4-2a in the pixel a and to a Purkinje detection mode M4-2b in the pixel b at a moment when the intensity changes from the low intensity S1-9 to the high intensity S2-9, and subsequently, a transition is made to an event mode M1-28 in a state where the intensity is constant at the high intensity S2-9. A transition is made from the event mode M1-28 to a pupil detection mode M4-3a in the pixel a and to a Purkinje detection mode M4-3b in the pixel b at a moment when the intensity changes from the high intensity S2-9 to the low intensity S1-9, and a transition is made from the pupil detection mode M4-3a and the Purkinje detection mode M4-3b to an event mode M1-29 in a state where the intensity is constant at the low intensity S1-9.

As illustrated in the transition pattern 109, it is possible to generate the three modes by arranging the pixels a and b having two different thresholds in the Bayer array with the two intensities (low intensity S1-9 and high intensity S2-9).

The above is summarized as follows.

Pixel a (having lower threshold): Generation of pupil detection mode and event mode.

Pixel b (having higher threshold): Generation of Purkinje detection mode and event mode.

As described above, contents that have been described regarding the line-of-sight detection device and the method for sensing an eyeball in the ninth embodiment (Example 9 of the line-of-sight detection device and Example 9 of the method for sensing an eyeball) according to the present technology can be applied to the line-of-sight detection devices and the methods for sensing an eyeball in the first to eighth embodiments according to the present technology described above, and the line-of-sight detection device and the method for sensing an eyeball in the tenth embodiment according to the present technology as described later particularly as long as there is no technical contradiction.

11. Tenth Embodiment (Example 10 of Line-of-Sight Detection Device and Example 10 of Method for Sensing Eyeball)

The line-of-sight detection device in the tenth embodiment (Example 10 of the line-of-sight detection device) according to the present technology is a line-of-sight detection device including: an imaging element (for example, a dynamic vision sensor (DVS)) having an event-driven function; a first mode generation unit that generates a Purkinje detection mode; a second mode generation unit that generates a pupil detection mode; and a third mode generation unit that generates an event-driven mode, and further includes a light emitting device. The imaging element having the event-driven function provided in the line-of-sight detection device in the tenth embodiment according to the present technology has two thresholds with change of time. Then, the light emitting device provided in the line-of-sight detection device in the tenth embodiment according to the present technology has two light emission intensities.

The method for sensing an eyeball in the tenth embodiment (Example 10 of the method for sensing an eyeball) according to the present technology is a method for sensing an eyeball including: by using an imaging element having an event-driven function, generating a Purkinje detection mode, generating a pupil detection mode, and generating an event-driven mode; and transitioning to the Purkinje detection mode, transitioning to the pupil detection mode, and transitioning to the event-driven mode, and further includes changing to two light emission intensity states using a light emitting device. An imaging element having an event-driven function used in the method for sensing an eyeball in the ninth embodiment according to the present technology has two thresholds based on a temporal change. Meanwhile, the method for sensing an eyeball in the tenth embodiment (Example 10 of the method for sensing an eyeball) according to the present technology may be executed using the line-of-sight detection device in the tenth embodiment (Example 10 of the line-of-sight detection device) according to the present technology.

The line-of-sight detection device and the method for sensing an eyeball in the tenth embodiment according to the present technology will be described with reference to FIG. 13.

Figure 13:
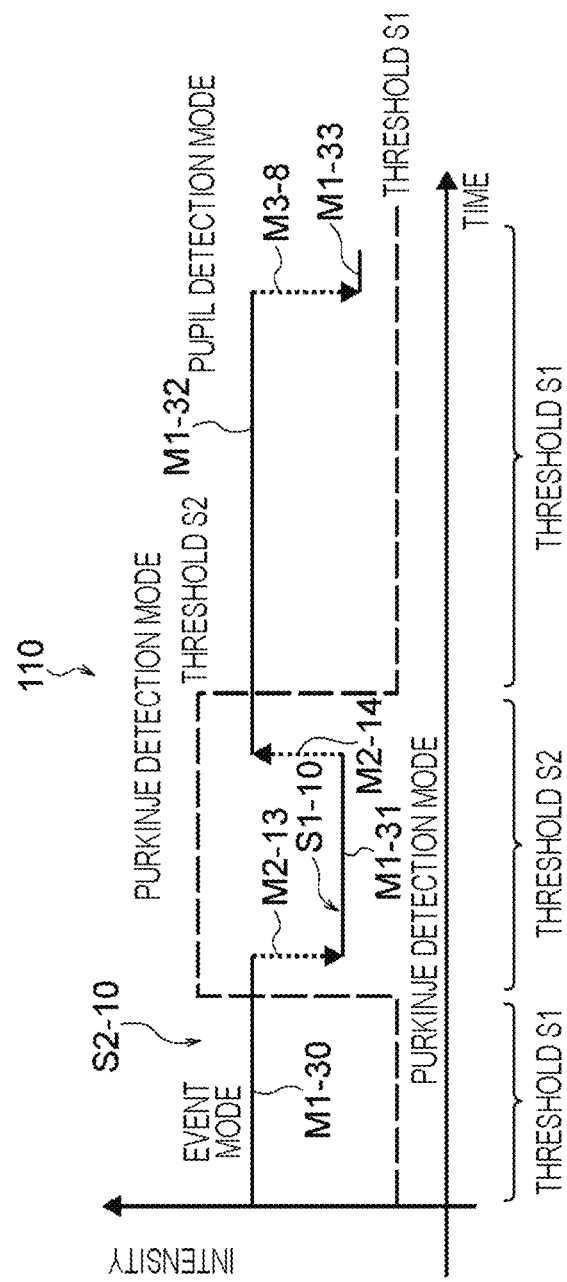
FIG. 13 is a view illustrating an example of a transition method of three modes (event-driven mode, Purkinje detection mode, and pupil detection mode) in a line-of-sight detection device and a method for sensing an eyeball in a tenth embodiment to which the present technology is applied.

FIG. 13 is a view illustrating an example of a transition method of three modes (the event-driven mode, the Purkinje detection mode, and the pupil detection mode) in the line-of-sight detection device and the method for sensing an eyeball in the ninth embodiment according to the present technology. More specifically, FIG. 13 is a view illustrating a transition pattern 110 of three modes (Purkinje detection mode, pupil detection mode, and event-driven mode) when a threshold is changed from a threshold S1 to a threshold S2 (>threshold S1, that is, the threshold S2 is higher than the threshold S1) and then changed from the threshold S2 (>threshold S1) to the threshold S1 with a lapse of time.

In the transition pattern 110, a transition is made from an event mode M1-30 in a state where the intensity is constant at a high intensity S2-10 when the threshold S1 changes to the threshold S2 (at this time, the threshold S1 changes to the threshold S2) to a Purkinje detection mode M2-13 at a moment when the intensity changes from the high intensity S2-10 to a low intensity S1-10 (at this time, the threshold S2 is applied), and subsequently, a transition is made from the Purkinje detection mode M2-13 to an event mode M1-31 in a state where the intensity is constant at the low intensity S1-10 (at this time, the threshold S2 is applied). Next, a transition is made from the event mode M1-31 to a Purkinje detection mode M2-14 that is a moment when the intensity changes from the low intensity S1-10 to the high intensity S2-10 (at this time, the threshold S2 is applied), and subsequently, a transition is made to an event mode M1-32 in a state where the intensity is constant at the high intensity S2-10 (at this time, the threshold S2 changes to the threshold S1). A transition is made from the event mode M1-32 to a pupil detection mode M3-8 that is a moment when the intensity changes from the high intensity S2-10 to the low intensity S1-10 (at this time, the threshold S1 is applied), and a transition is made from the pupil detection mode M3-8 to an event mode M1-33 in a state where the intensity is constant at the low intensity S1-10 (at this time, the threshold S1 is applied).

As illustrated in the transition pattern 110, the three modes can be generated by changing the two different thresholds over time with the two intensities (low intensity S1-10 and high intensity S2-10).

The above is summarized as follows.

Low threshold (threshold S1): Generation of pupil detection mode and event mode.

High threshold (threshold S2): Generation of Purkinje detection mode.

As described above, contents that have been described regarding the line-of-sight detection device and the method for sensing an eyeball in the tenth embodiment (Example 10 of the line-of-sight detection device and Example 10 of the method for sensing an eyeball) according to the present technology can be applied to the line-of-sight detection devices and the methods for sensing an eyeball in the first to ninth embodiments according to the present technology described above particularly as long as there is no technical contradiction.

12. Eleventh Embodiment (Example 1 of Display Device)

A display device of an eleventh embodiment (Example 1 of the display device) according to the present technology is a display device including at least a line-of-sight detection device of one embodiment among the line-of-sight detection devices of the first to tenth embodiments according to the present technology. The display device of the eleventh embodiment according to the present technology can be applied to, for example, an eyewear display, a head-mounted display, and the like.

Figure 15:
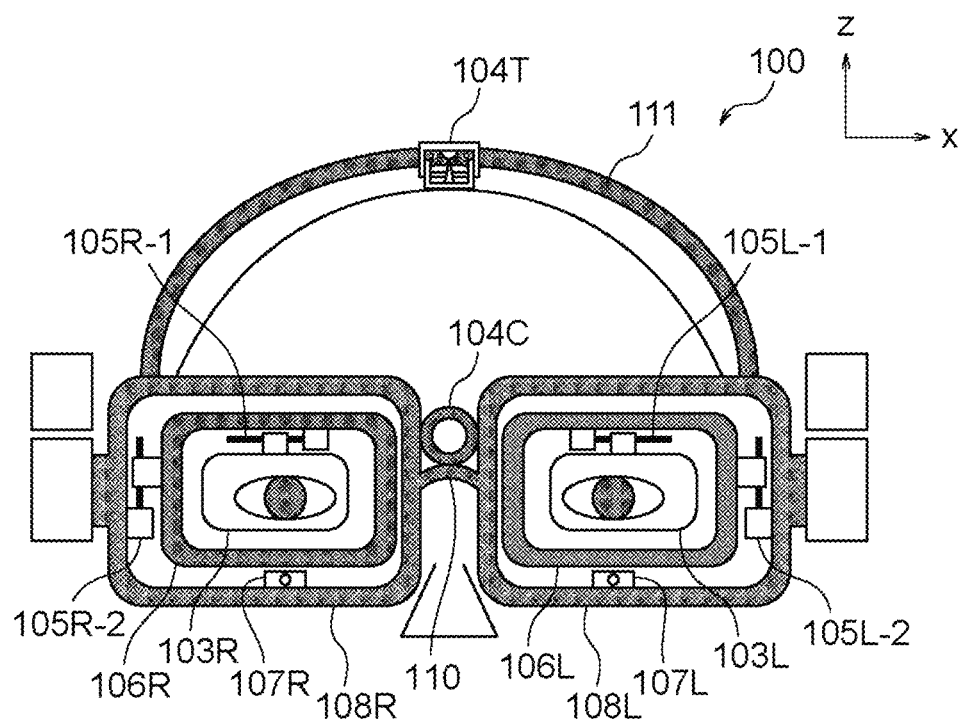
FIG. 15 is a front view illustrating the configuration example of the display device in the eleventh embodiment to which the present technology is applied.
Figure 16:
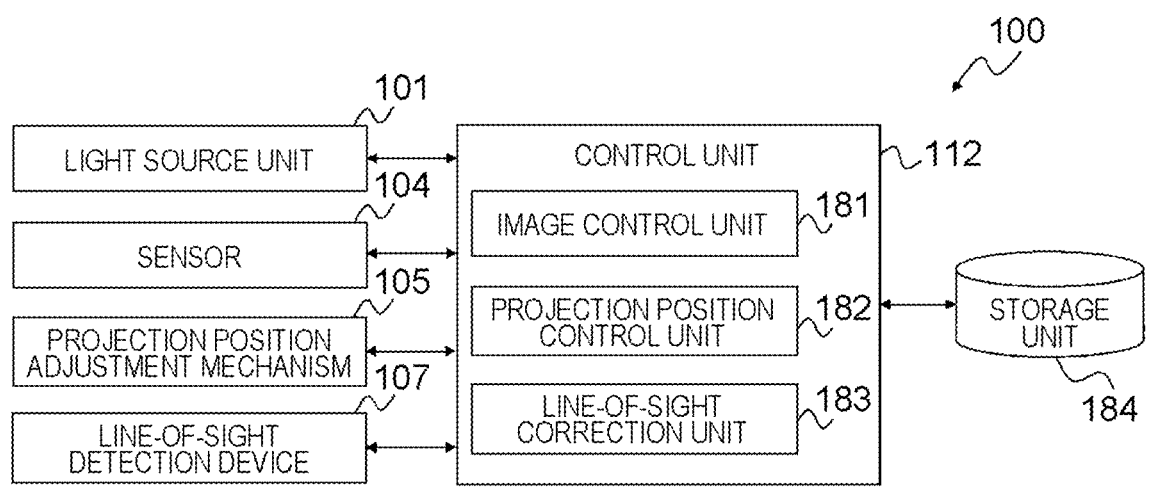
FIG. 16 is a block diagram illustrating the configuration example of the display device in the eleventh embodiment to which the present technology is applied.

Hereinafter, the display device of the eleventh embodiment (Example 1 of the display device) according to the present technology will be described with reference to FIGS. 14 to 16.

First, a configuration example of the display device of the eleventh embodiment according to the present technology will be described with reference to FIGS. 14 and 15. FIG. 14 is a top view of the display device according to the present technology in a state of being worn on a head of a user. FIG. 15 is a front view of the display device according to the present technology in the state of being worn on the head of the user. The display device illustrated in FIG. 14 includes: a video display unit (also referred to as an image display unit); a sensor that detects a positional change of the display device with respect to the head (the sensor that detects the positional change of the display device with respect to the head is also referred to as a "displacement sensor" or a "sensor" in the present specification); a line-of-sight detection device (a line-of-sight detection device of one embodiment among the line-of-sight detection devices in the first to tenth embodiments according to the present technology, and the same applies hereinafter); a projection position adjustment mechanism; a control unit; and a storage unit. These constituent elements will be described hereinafter.

(Video Display Unit)

Figure 14:
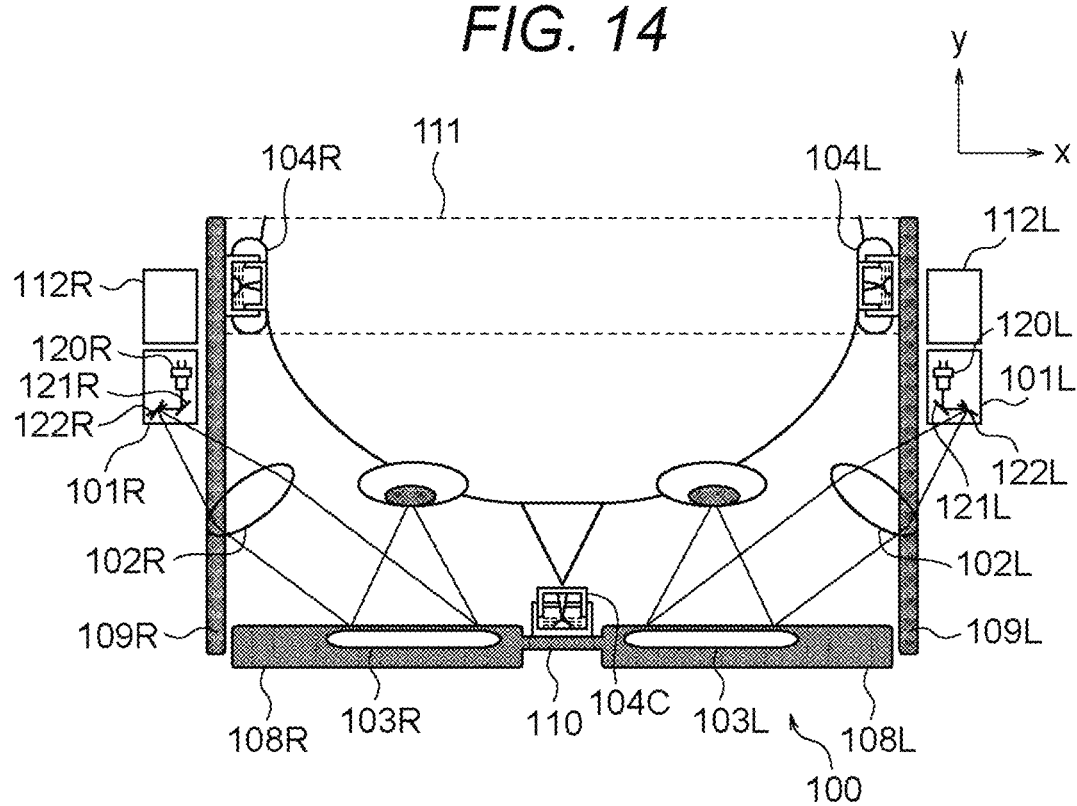
FIG. 14 is a top view illustrating a configuration example of a display device in an eleventh embodiment to which the present technology is applied.

As illustrated in FIG. 14, a display device 100 has a glasses-like shape, and is configured to project video display light (sometimes referred to as image display light) to each of both eyes. That is, the display device 100 includes a video display unit that projects video display light to the left eye and a video display unit that projects video display light to the right eye. The video display unit that projects the video display light to the left eye includes a light source unit 101L, a projection optical system 102L, and a holographic optical element (hereinafter, also referred to as HOE) 103L.

The light source unit 101L emits video display light. As a configuration for emitting the video display light, the light source unit 101L can include, for example, a laser light source 120L, a mirror 121L, and a scanning mirror 122L. Laser light emitted from the laser light source 120L is reflected by the mirror 121L, and then, reaches the scanning mirror 122L. The scanning mirror 122L two-dimensionally scans the laser light. The scanning mirror 122L may be, for example, a MEMS mirror. The scanning mirror 122L can move a direction of the laser light at a high speed such that an image is formed on a retina.

The projection optical system 102L adjusts a direction of the video display light such that the video display light reaches a desired region and/or position of the HOE 103L. For example, the video display light scanned by the scanning mirror 122L is adjusted to be parallel light.

The HOE 103L diffracts the video display light to be condensed near a pupil of the user and emitted to the retina. The HOE 103L may be, for example, a reflection-type diffraction element. The HOE 103L may have optical characteristics of functioning as a lens for light having a wavelength range of the video display light and transmitting light having a wavelength outside the wavelength range. With the optical characteristics, the user can recognize, for example, a landscape ahead in a line-of-sight direction via the HOE 103L and can recognize an image of the video display light. That is, the image of the video display light can be superimposed on the landscape of the outside world. As the HOE 103L, a hologram lens, preferably a film-shaped hologram lens, and more preferably a transparent film-shaped hologram lens can be used. The film-shaped hologram lens may be used by being pasted to, for example, glass or the like. Desired optical characteristics can be imparted to the hologram lens by techniques known in the art. Then, a commercially available hologram lens may be used as the hologram lens, or the hologram lens may be manufactured by techniques known in the art.

As described above, the light source unit 101L, the projection optical system 102L, and the HOE 103L cause the video display light to reach the left eye of the user.

The display device 100 includes a temple portion 109L and a rim portion 108L each of which is a part of the glasses shape. The light source unit 101L and the projection optical system 102L are arranged on the temple portion 109L. The HOE 103L is held by the rim portion 108L. More specifically, an inner rim portion 106L is held by the rim portion 108L via a projection position adjustment mechanism 105L-2, and the HOE 103L is held by the inner rim portion 106L via a projection position adjustment mechanism 105L-1.

The video display unit that projects the video display light to the right eye of the user includes a light source unit 101R, a projection optical system 102R, and an HOE 103R.

The description regarding the light source unit 101L, the projection optical system 102L, and the HOE 103L also applies to the light source unit 101R, the projection optical system 102R, and the HOE 103R.

The light source unit 101R and the projection optical system 102R are arranged in a temple portion 109R similarly to the video display unit for the left eye. The HOE 103R is held by a rim portion 108R. More specifically, an inner rim portion 106R is held by the rim portion 108R via a projection position adjustment mechanism 105R-2, and the HOE 103R is held by the inner rim portion 106R via a projection position adjustment mechanism 105R-1.

The rim portions 108L and 108R of the display device 100 are connected to each other via a bridge portion 110. The bridge portion 110 is a portion that is put on a nose of the user when the user wears the display device 100. Furthermore, both the rim portions 108L and 108R of the display device 100 are connected to a headband portion 111. As illustrated in FIG. 15, the headband portion 111 is a portion that comes into contact with the top of the head of the user when the user wears the display device 100.

Although the light source unit 101L illustrated in FIG. 14 includes one laser light source 120L, the number of laser light sources included in the light source unit 101L may be two or more, and may be, for example, two to five. A plurality of these laser light sources may be configured to output beams of laser light having different wavelengths. Similarly, although the light source unit 101R includes one laser light source 120R, the number of laser light sources included in the light source unit 101R may be two or more, and may be, for example, two to five. A plurality of these laser light sources may be configured to output beams of laser light having different wavelengths. Since the laser light source 120L and the laser light source 120R are used, a stimulus of a specific wavelength can be presented.

The display device 100 may further include a wavelength dispersion compensation member although not illustrated. The wavelength dispersion compensation member is, for example, a reflection-type or transmission-type volume hologram, a reflection-type or transmission-type relief hologram, or the like. The wavelength dispersion compensation member may be disposed in the periphery of the mirror 121L and/or 121R, for example, between the mirror 121L and the scanning mirror 122L and/or between the mirror 121R and the scanning mirror 122R. When the wavelength dispersion compensation member is used in the display device 100, it is possible to accurately stimulate any point (predetermined point) on the retina since a wavelength dispersion is compensated.

(Sensor)

The display device 100 further includes sensors 104L, 104R, 104C, and 104T that detect a positional change of the display device 100 with respect to the head of the user. The positional change detected by these sensors may be, for example, a direction of the positional change and/or an amount of the positional change. Note that the sensors 104L, 104R, 104C, and 104T may be collectively referred to as a sensor 104 in the present specification.

The sensors 104L and 104R detect a positional change of the display device 100 with respect to the head of the user in a horizontal direction, the sensor 104C detects a positional change of the display device 100 with respect to the head of the user in a front-rear direction, and the sensor 104T detects a positional change of the display device 100 with respect to the head of the user in an up-down direction. Therefore, a mounting deviation can be three-dimensionally grasped.

(Line-of-Sight Detection Device)

The display device 100 includes line-of-sight detection devices 107L and 107R that detect a line of sight of the user. In the present specification, the line-of-sight detection devices 107L and 107R may be collectively referred to as a line-of-sight detection device 107. A line-of-sight detection device of one embodiment among the line-of-sight detection devices of the first to tenth embodiments according to the present technology described above can be applied to the line-of-sight detection device 107 (the line-of-sight detection devices 107L and 107R).

(Projection Position Adjustment Mechanism)

The projection position adjustment mechanisms 105L-1 and 105L-2 and 105R-1 and 105R-2 that adjust a projection position of video display light emitted from the display device 100 can be further included. Note that these four projection position adjustment mechanisms are sometimes collectively referred to as a projection position adjustment mechanism 105 in the present specification. The projection position adjustment mechanism 105 may be configured to adjust the projection position of the video display light to follow the line of sight, for example. The projection position adjustment mechanism 105 can adjust the projection position of the video display light in accordance with a mounting deviation.

In addition, the projection position adjustment mechanism 105 can adjust the projection position of the video display light in accordance with rotational movement of an eyeball or movement of the line of sight. For example, when the display device 100 includes the projection position adjustment mechanism 105, a position of an image that is presented to the user can be adjusted to a more appropriate position. For example, in a case where an image to be presented by the display device 100 is superimposed on an image of the outside world, it is possible to display the image at a more appropriate position by detecting the line of sight of the user. That is, it is preferable to include the line-of-sight detection device 107 in terms of presentation of AR information. Furthermore, it is also possible to adjust a position where the video display light is condensed in image display in a Maxwell view by these projection position adjustment mechanisms.

The projection position adjustment mechanisms 105L-1 and 105L-2 adjust the projection position of the video display light projected on the left eye. The projection position adjustment mechanism 105L-1 adjusts a positional relationship between the inner rim portion 106L and the rim portion 108L in a z-axis direction. For example, the projection position adjustment mechanism 105L-1 moves the inner rim portion 106L in the z-axis direction with respect to the rim portion 108L. Therefore, a position of the HOE 103L in the z-axis direction is adjusted. The projection position adjustment mechanism 105L-2 adjusts a positional relationship between the HOE 103L and the inner rim portion 106L in an x-axis direction. For example, the projection position adjustment mechanism 105L-2 moves the HOE 103L in the x-axis direction with respect to the inner rim portion 106L. Therefore, a position of the HOE 103L in the x-axis direction is adjusted.

A driving element configured to drive the adjustment of the positional relationship between the inner rim portion 106L and the rim portion 108L in the z-axis direction by the projection position adjustment mechanism 105L-1 may be, for example, a piezo element, an actuator, or bimetal, but is not limited thereto. A driving element configured to the adjustment of the positional relationship between the HOE 103L and the inner rim portion 106L in the x-axis direction by the projection position adjustment mechanism 105L-2 may also be, for example, a piezo element, an actuator, or bimetal, but is not limited thereto.

The projection position adjustment mechanism 105L-1 can adjust the positional relationship between the inner rim portion 106L and the rim portion 108L in the z-axis direction on the basis of, for example, a positional change of the display device 100 detected by one, two, three, or all four of the sensors 104L, 104R, 104C, and 104T. Furthermore, the projection position adjustment mechanism 105L-1 may adjust the positional relationship on the basis of the positional change and the line of sight detected by the line-of-sight detection device 107L. The projection position adjustment mechanism 105L-2 can adjust the positional relationship between the HOE 103L and the inner rim portion 106L in the x-axis direction on the basis of, for example, a positional change of the display device 100 detected by one, two, three, or all four of the sensors 104L, 104R, 104C, and 104T. Furthermore, the projection position adjustment mechanism 105L-2 may adjust the positional relationship on the basis of the positional change and the line of sight detected by the line-of-sight detection device 107L.

The projection position adjustment mechanisms 105R-1 and 105R-2 adjust the projection position of the video display light projected on the right eye. The adjustment may be performed similarly to that of the projection position adjustment mechanisms 105L-1 and 105L-2.

(Control Unit and Storage Unit)

A description will be given with reference to FIG. 16. The display device 100 includes a control unit 112. As illustrated in FIG. 16 which is a block diagram illustrating main components of the display device 100, the control unit 112 includes an image control unit 181, a projection position control unit 182, and a line-of-sight correction unit 183.

The image control unit 181 controls projection of image display light by the image display unit. The image control unit 181 drives, for example, the light source units 101L and 101R, particularly, the laser light sources and the scanning mirrors included in these light source units to output image display light. The image control unit 181 can acquire image data stored in a storage unit 184, for example, and can cause the light source units 101L and 101R to output the image display light on the basis of the image data. The image control unit 181 may correct the image data on the basis of a positional change, detected by the sensor 104, of the display device 100 with respect to the head. The image control unit 181 may cause the light source units 101L and 101R to output the image display light on the basis of the corrected image data. That is, the display device 100 may correct an image on the basis of the positional change detected by the sensor that detects a positional change of a head-mounted display device with respect to the head.

The projection position control unit 182 controls the projection position adjustment mechanisms 105L-1, 105L-2, 105R-1, and 105R-2, whereby a projection position of the image display light can be controlled. For example, the projection position control unit 182 can drive one to four of the projection position adjustment mechanisms 105L-1, 105L-2, 105R-1, and 105R-2 on the basis of a line of sight detected by the line-of-sight detection devices 107L and 107R to adjust the projection position of the image display light. For example, the projection position of the image display light can be adjusted so as to follow the line of sight.

The projection position control unit 182 may adjust the projection position of the image display light by driving one to four of the projection position adjustment mechanisms 105L-1, 105L-2, 105R-1, and 105R-2 on the basis of the line of sight corrected by the line-of-sight correction unit 183 as described later. For example, the projection position of the image display light can be adjusted so as to follow the corrected line of sight. The projection position control unit 182 may adjust the projection position of the image display light by driving one to four of the projection position adjustment mechanisms 105L-1, 105L-2, 105R-1, and 105R-2 on the basis of data (hereinafter also referred to as "displacement data") regarding the positional change of the display device 100 with respect to the head detected by one to four of the sensors 104L, 104R, 104C, and 104T.

For example, the projection position control unit 182 can calculate a position adjustment amount obtained by each of the projection position adjustment mechanisms on the basis of the displacement data and a correction coefficient. The projection position control unit 182 can drive each of the projection position adjustment mechanisms such that a positional relationship is changed by the calculated position adjustment amount. The projection position control unit 182 may acquire a correction coefficient from a correction table stored in advance in the storage unit 184, for example, and use the correction coefficient for the calculation of the position adjustment amount. The correction table may include, for example, a plurality of correction coefficients, and the projection position control unit 182 can select a predetermined correction coefficient in accordance with the displacement data from among the plurality of correction coefficients. Furthermore, the correction table may be provided for each of the projection position adjustment mechanisms, for example. The correction table may be provided in advance in the display device 100, or may be updated according to use of the display device 100 by the user. The accuracy of projection position control can be improved by selecting or updating the correction table or the correction coefficient. The projection position control unit 182 may use the line of sight detected by the line-of-sight detection device or the line of sight corrected by the line-of-sight correction unit 183 in order to calculate the position adjustment amount.

The line-of-sight correction unit 183 corrects the line of sight detected by the line-of-sight detection devices 107L and 107R on the basis of the displacement data. Therefore, the line-of-sight correction unit 183 can identify a line of sight in consideration of a mounting deviation, and the line-of-sight detection accuracy is improved. The correction may be performed with respect to an optical axis of an eyeball, may be performed on a visual axis of the eyeball, or may be performed with respect to another reference axis. The line-of-sight correction unit 183 may also acquire a correction coefficient from a correction table stored in advance in the storage unit 184, for example, and use the correction coefficient for the line-of-sight correction. The correction table may include, for example, a plurality of correction coefficients, and the line-of-sight correction unit 183 may select a predetermined correction coefficient in accordance with the displacement data from among the plurality of correction coefficients. The correction table may be provided in advance in the display device 100, or may be updated according to use of the display device 100 by the user. The accuracy of the line-of-sight correction can be improved by selecting or updating the correction table or the correction coefficient.

The display device 100 may further include the storage unit 184. The storage unit may store data related to the image display light projected by the image display unit, the correction table used for the projection position control performed by the projection position control unit 122, and the correction table used for the line-of-sight correction performed by the line-of-sight correction unit 123.

Note that embodiments according to the present technology are not limited to the respective embodiments described above, and various modifications can be made within a scope not departing from a gist of the present technology.

Furthermore, the effects described in the present specification are merely examples and are not limited, and there may be other effects.

Furthermore, the present technology can also have the following configurations.

[1]

A line-of-sight detection device including:
an imaging element having an event-driven function;
a first mode generation unit that generates a Purkinje detection mode;
a second mode generation unit that generates a pupil detection mode; and
a third mode generation unit that generates an event-driven mode.

[2]

The line-of-sight detection device according to [1], further including
a light emitting device,
in which the light emitting device has three light emission intensities.

[3]

The line-of-sight detection device according to [1], further including
a light emitting device,
in which the light emitting device has two light emission intensities,
the imaging element having the event-driven function includes a first pixel and a second pixel having mutually different thresholds, and
the first pixel and the second pixel are arranged in a Bayer array.

[4]

The line-of-sight detection device according to [1], further including
a light emitting device,
in which the light emitting device has two light emission intensities, and
the imaging element having the event-driven function has two thresholds with change of time.

[5]

The line-of-sight detection device according to any one of [1] to [4], further including
a plurality of light emitting devices,
in which the first mode generation unit generates the Purkinje detection mode when each of the plurality of light emitting devices is sequentially turned on.

[6]

The line-of-sight detection device according to any one of [1] to [5], further including
a light emitting device,
in which the light emitting device has three light emission intensities,
the three light emission intensities are a high intensity, a medium intensity, and a low intensity, and an intensity difference between the high intensity and the medium intensity is substantially identical to an intensity difference between the medium intensity and the low intensity.

[7]
The line-of-sight detection device according to any one of [1] to [6], further including
a plurality of light emitting devices,
in which the second mode generation unit generates the pupil detection mode when the plurality of light emitting devices changes light emission intensities substantially simultaneously.

[8]
The line-of-sight detection device according to any one of [1] to [7], further including: a light emitting device; and a signal acquisition unit,
in which the signal acquisition unit
acquires a signal in synchronization with a time stamp of a change in a light emission intensity of the light emitting device in the Purkinje detection mode and the pupil detection mode, and
performs time stamp accumulation to acquire a signal in the event-driven mode.

[9]
The line-of-sight detection device according to any one of [1] to [8], in which
the second mode generation unit generates the pupil detection mode when detection is lost in the event-driven mode.

[10]
The line-of-sight detection device according to any one of [1] to [9], in which
the second mode generation unit generates the pupil detection mode when a detection likelihood of the event-driven mode is less than a predetermined value.

[11]
The line-of-sight detection device according to any one of [1] to [10], in which
the second mode generation unit generates the pupil detection mode when an end of a saccade is detected in the event-driven mode.

[12]
A display device including at least the line-of-sight detection device according to any one of [1] to [11].

[13]
A method for sensing an eyeball including:
by using an imaging element having an event-driven function,
generating a Purkinje detection mode, generating a pupil detection mode, and generating an event-driven mode; and
transitioning to the Purkinje detection mode, transitioning to the pupil detection mode, and transitioning to the event-driven mode.

[14]
The method for sensing an eyeball according to [13], further including changing to three light emission intensity states using a light emitting device.

[15]
The method for sensing an eyeball according to [13], further including
changing to two light emission intensity states using a light emitting device,
in which the imaging element having the event-driven function includes a first pixel and a second pixel which have different thresholds, and the first pixel and the second pixel are arranged in a Bayer array.

[16]
The method for sensing an eyeball according to [13], further including
changing to two light emission intensity states using a light emitting device,
in which the imaging element having the event-driven function has two thresholds with change of time.

[17]
The method for sensing an eyeball according to any one of [13] to [16], further including sequentially transitioning to the Purkinje detection mode by sequentially turning on each of a plurality of light emitting devices using the plurality of light emitting devices.

[18]
The method for sensing an eyeball according to any one of [13] to [17], further including
changing to three light emission intensity states using a light emitting device,
in which the three light emission intensities are a high intensity, a medium intensity, and a low intensity, and
an intensity difference between the high intensity and the medium intensity is substantially identical to an intensity difference between the medium intensity and the low intensity.

[19]
The method for sensing an eyeball according to any one of [13] to [18], further including substantially simultaneously changing light emission intensities of a plurality of light emitting devices using the plurality of light emitting devices to transition to the pupil detection mode.

[20]
The method for sensing an eyeball according to any one of [13] to [19], further including:
acquiring a signal in synchronization with a time stamp of a change in a light emission intensity of a light emitting device in the Purkinje detection mode and the pupil detection mode; and
performing time stamp accumulation to acquire a signal in the event-driven mode.

[21]
The method for sensing an eyeball according to any one of [13] to [20], further including
transitioning to the pupil detection mode when detection is lost in the event-driven mode.

[22]
The method for sensing an eyeball according to any one of [13] to [21], further including
transitioning to the pupil detection mode when a detection likelihood of the event-driven mode is less than a predetermined value.

[23]
The method for sensing an eyeball according to any one of [13] to [22], further including
transitioning to the pupil detection mode when an end of a saccade is detected in the event-driven mode.

REFERENCE SIGNS LIST

41 Purkinje image
43 Boundary (edge) between pupil and iris
44 Boundary (edge) between iris and sclera
45 Pupil
46 Iris
47 Sclera 102, 103, 103-1, 104-1, 104-2, 104-3, 105-1, 105-2, 105-3, 109, 110 Transition pattern
100 Display device
1000 Intensity pattern of reflected light of eye
1001 Intensity pattern of reflected light of eye in event-driven mode
1002 Intensity pattern of reflected light of eye in Purkinje detection mode
1003 Intensity pattern of reflected light of eye in pupil detection mode

The invention claimed is:

1. A line-of-sight detection device, comprising:
an imaging element having an event-driven function;
a first mode generation unit configured to generate a Purkinje detection mode;
a second mode generation unit configured to generate a pupil detection mode;
a third mode generation unit configured to generate an event-driven mode; and
a light emitting device that has two light emission intensities, wherein
the imaging element having the event-driven function has two thresholds with change of time.

2. The line-of-sight detection device according to claim 1, wherein the light emitting device has three light emission intensities.

3. The line-of-sight detection device according to claim 1, wherein
the imaging element having the event-driven function includes a first pixel and a second pixel which have different thresholds, and
the first pixel and the second pixel are arranged in a Bayer array.

4. The line-of-sight detection device according to claim 1, further comprising
a plurality of light emitting devices,
wherein the first mode generation unit is further configured to generate the Purkinje detection mode based on each of the plurality of light emitting devices that is sequentially turned on.

5. The line-of-sight detection device according to claim 1, wherein
the light emitting device has three light emission intensities,
the three light emission intensities are a high intensity, a medium intensity, and a low intensity, and
an intensity difference between the high intensity and the medium intensity is substantially identical to an intensity difference between the medium intensity and the low intensity.

6. The line-of-sight detection device according to claim 1, further comprising
a plurality of light emitting devices,
wherein the second mode generation unit is further configured to generate the pupil detection mode based on the plurality of light emitting devices that changes light emission intensities of the plurality of light emitting devices substantially simultaneously.

7. The line-of-sight detection device according to claim 1, further comprising
a signal acquisition unit configured to:
acquire a signal in synchronization with a time stamp of a change in a light emission intensity of the two light emission intensities of the light emitting device in the Purkinje detection mode and the pupil detection mode; and
perform time stamp accumulation to acquire a signal in the event-driven mode.

8. The line-of-sight detection device according to claim 1, wherein
the second mode generation unit is further configured to generate the pupil detection mode based on loss of detection in the event-driven mode.

9. The line-of-sight detection device according to claim 1, wherein
the second mode generation unit is further configured to generate the pupil detection mode based on a detection likelihood of the event-driven mode that is less than a specific value.

10. The line-of-sight detection device according to claim 1, wherein
the second mode generation unit is further configured to generate the pupil detection mode based on detection of an end of a saccade in the event-driven mode.

11. A display device, comprising
a line-of-sight detection device comprising:
an imaging element having an event-driven function;
a first mode generation unit configured to generate a Purkinje detection mode;
a second mode generation unit configured to generate a pupil detection mode;
a third mode generation unit configured to generate an event-driven mode; and
a light emitting device, wherein the light emitting device that has two light emission intensities, wherein
the imaging element having the event-driven function has two thresholds with change of time.

12. A method for sensing an eyeball, the method comprising:
by using an imaging element having an event-driven function:
generating a Purkinje detection mode, generating a pupil detection mode, and generating an event-driven mode; and
transitioning to the Purkinje detection mode, transitioning to the pupil detection mode, and transitioning to the event-driven mode; and
changing to two light emission intensity states using a light emitting device, wherein
the imaging element having the event-driven function includes a first pixel and a second pixel which have different thresholds, and
the first pixel and the second pixel are arranged in a Bayer array.

13. The method for sensing the eyeball according to claim 12, further comprising changing to three light emission intensity states using the light emitting device.

14. The method for sensing the eyeball according to claim 12, further comprising
sequentially transitioning to the Purkinje detection mode by sequentially turning on each of a plurality of light emitting devices.

15. The method for sensing the eyeball according to claim 12, further comprising
changing to three light emission intensity states using the light emitting device, wherein
the three light emission intensity states include three light emission intensities,
the three light emission intensities are a high intensity, a medium intensity, and a
low intensity, and an intensity difference between the high intensity and the medium intensity is substantially identical to an intensity difference between the medium intensity and the low intensity.

16. The method for sensing the eyeball according to claim 12, further comprising transitioning to the pupil detection mode based on substantially simultaneously changing light emission intensities of a plurality of light emitting devices.

17. The method for sensing the eyeball according to claim 12, further comprising:

acquiring a signal in synchronization with a time stamp of a change in a light emission intensity of two light emission intensities of the light emitting device in the Purkinje detection mode and the pupil detection mode; and performing time stamp accumulation to acquire a signal in the event-driven mode.

18. The method for sensing the eyeball according to claim 12, further comprising transitioning to the pupil detection mode based on loss of detection in the event-driven mode.

19. The method for sensing the eyeball according to claim 12, further comprising transitioning to the pupil detection mode based on a detection likelihood of the event-driven mode that is less than a specific value.

20. The method for sensing the eyeball according to claim 12, further comprising transitioning to the pupil detection mode based on detection of an end of a saccade in the event-driven mode.

21. A line-of-sight detection device, comprising:

an imaging element having an event-driven function;

a first mode generation unit configured to generate a Purkinje detection mode;

a second mode generation unit configured to generate a pupil detection mode;

a third mode generation unit configured to generate an event-driven mode; and a light emitting device that has three light emission intensities.

22. A method for sensing an eyeball, the method comprising:

by using an imaging element having an event-driven function:

generating a Purkinje detection mode, generating a pupil detection mode, and generating an event-driven mode; and transitioning to the Purkinje detection mode, transitioning to the pupil detection mode, and transitioning to the event-driven mode; and changing to three light emission intensity states using a light emitting device.

* * * * *